US007060429B2

(12) United States Patent
Krueger et al.

(10) Patent No.: US 7,060,429 B2
(45) Date of Patent: Jun. 13, 2006

(54) TREATMENT OF NEURODEGENERATIVE DISEASES BY ALTERING LEVELS OF TRKB ISOFORMS AND/OR TRKC ISOFORMS

(75) Inventors: Bruce K. Krueger, Ellicott City, MD (US); Tami J. Kingsbury, Baltimore, MD (US); Linda L. Bambrick, Baltimore, MD (US); Susan G. Dorsey, Frederick, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 27 days.

(21) Appl. No.: 10/645,546

(22) Filed: Aug. 22, 2003

(65) Prior Publication Data

US 2004/0110711 A1 Jun. 10, 2004

Related U.S. Application Data

(63) Continuation of application No. PCT/US02/16807, filed on May 28, 2002, and a continuation of application No. PCT/US02/05151, filed on Feb. 22, 2002.

(60) Provisional application No. 60/270,553, filed on Feb. 22, 2001.

(51) Int. Cl.
*A01N 43/04* (2006.01)
*A61K 31/175* (2006.01)

(52) U.S. Cl. ........................ 435/4; 435/320.1; 435/325

(58) Field of Classification Search .................. 514/44
See application file for complete search history.

(56) References Cited

OTHER PUBLICATIONS

Peltekian E, Adenovirus-mediated gene transfer to the brain: methodological assessment, 1997, Journal of Neuroscience Methods, 71, 77-84.*

Somia N, Gene therapy: trials and tribulaions, 2000, Nature Reviews Genetics 1, 91-99.*

Kennedy PGE, Potential use of herpes simplex virus (HSV) vectors for gene therapy of neurological disorders, 1997, Brain, 120, 1245-1259.*

Klau M, Reduced number of functional glutamatergic synapses in hippocampal neurons overexpressing full-length TrkB receptors, 2001, J. of Neuroscience Research, 66, 327-336.*

Bambrick LL, Glutamate as a hippocampal neuron survival factor: An inherited defect in the trisomy 16 mouse, 1995, PNAS, vol. 92, pp. 9692-9696.*

Notification of Transmittal of International Preliminary Examination Report issued in corresponding PCT US/02/0515.

* cited by examiner

*Primary Examiner*—Deborah Crouch
*Assistant Examiner*—David A. Montanari
(74) *Attorney, Agent, or Firm*—Buchanan Ingersoll PC

(57) ABSTRACT

This invention relates to a method of treating or preventing neuro-degenerative disorders and neuro-developmental disorders by altering the ratio of the amount of full-length TrkB polypeptide to the amount of truncated TrkB polypeptides in a neuron or by altering the ratio of the amount of full-length TrkC polypeptide to the amount of truncated TrkC polypeptides in a neuron.

8 Claims, 3 Drawing Sheets

TREATMENT OF NEURODEGENERATIVE DISEASES BY ALTERING LEVELS OF TRKB ISOFORMS AND/OR TRKC ISOFORMS

CROSS REFERENCE TO RELATED APPLICATIONS

This application is a continuation and claims priority under 35 U.S.C. §§ 119 and/or 365 to PCT/US02/16807, filed on May 28, 2002; PCT/US02/05151 filed on Feb. 22, 2002; and to U.S. Provisional Application No. 60/270,553 filed on Feb. 22, 2001, the entire contents of which are hereby incorporated by reference in their entireties for all purposes.

This research was funded in part by grants from the NIH (grant numbers AG10686 and NS40491). The federal government has certain rights to this invention.

BACKGROUND OF THE INVENTION

1. Field of Invention

This invention relates to a method for treating or preventing neuro-degenerative disorders and neuro-developmental disorders such as Alzheimer's disease, Parkinson's disease, Huntington's disease, amyotrophic lateral sclerosis (Lou Gehrig's disease) and the adverse neurologic complications of Down syndrome, as well as neuron death resulting from injury such as stroke, cerebral ischemia, or chemical and/or physical trauma to the central or peripheral nervous system. This invention further relates to the method of increasing the amount of the full-length TrkB isoform polypeptide in neurons to treat or prevent neuro-degenerative disorders and adverse neurologic complications of Down syndrome. This invention also relates to the method of decreasing the amount of the truncated TrkB isoform polypeptide in neurons to treat or prevent neuro-degenerative disorders, as well as the adverse neurologic complications of Down syndrome.

2. Description of the Related Art

Neurotrophins comprise a class of polypeptide neuron survival factors that not only support the survival of post-mitotic neurons (Lewin and Barde, Physiology of the neurotrophins; *Ann. Rev. Neurosci.* 19:289–317 (1996)), but also regulate other neuronal functions, including, among others, axon growth and synaptic plasticity (Black I B, Trophic regulation of synaptic plasticity; *J. Neurobiol.* 41:108–118 (1999); Lentz; et al., Neurotrophins support the development of diverse sensory axon morphologies; *J. Neurosci.* 19:1038–1048 (1999); Lu and Chow, Neurotrophins and hippocampal synaptic transmission and plasticity; *J. Neurosci. Res.* 58:76–87 (1999); McAllister et al., Neurotrophins and synaptic plasticity, *Ann. Rev. Neurosci.* 22:295–318 (1999); Schinder and Poo, The neurotrophin hypothesis for synaptic plasticity, *Trends Neurosci.* 23:639–645 (2000); Thoenen, Neurotrophins and activity-dependent plasticity, *Prog. Brain Res.* 128:183–191 (2000)). The class of neurotrophins includes, but is not limited to, nerve growth factor (NGF), brain derived neurotrophic factor (BDNF), neurotrophin-3 (NT-3), and neurotrophin-4/5 (NT-4/5). Neurotrophins bind to receptors and activate tyrosine receptor kinases (trks) (Barbacid, The Trk family of neurotrophin receptors, *J. Neurobiol.* 25:1386–1403 (1994); Bothwell, Functional interactions of neurotrophins and neurotrophin receptors, *Ann. Rev. Neurosci.* 18:223–253 (1995)). NGF primarily acts via TrkA; BDNF and NT-4/5 primarily via TrkB; and NT-3 primarily via TrkC. However the specificity of these interactions are not absolute. Binding of neurotrophins to trk dimers initiates trans auto-phosphorylation of specific tyrosine residues on the intracellular domain of the receptor (Segal and Greenberg, Intracellular signaling pathways activated by neurotrophic factors, *Ann. Rev. Neurosci.* 19:463–489 (1996); Kaplan and Miller, Neurotrophin signal transduction in the nervous system, *Curr. Opinion Neurobiol.* 10:381–391 (2000)). These phosphotyrosine residues serve as docking sites for elements of intracellular signaling cascades that lead to the suppression of neuron death and other effects of the neurotrophins. TrkB and TrkC are also present as truncated forms which lack the intracellular kinase domain and are, therefore, incapable of normal phosphorylation (Klein et al., The trkB tyrosine protein kinase gene codes for a second neurogenic receptor that lacks the catalytic kinase domain, *Cell* 61:647–656 (1990); Middlemas et al., trkB, a neural receptor protein-tyrosine kinase: evidence for a full-length and two truncated receptors, *Mol. Cell Biol.* 11:143–153 (1991); Tsoulfas et al., The rat trkC locus encodes multiple neurogenic receptors that exhibit differential response to neurotrophin-3 in PC12 cells, *Neuron* 10:975–990 (1993)). The full-length and truncated trk isoforms are generated by alternative splicing of the primary trk RNA. While there is some evidence that activation of truncated trk receptors can elicit cellular responses independently of normal tyrosine phosphorylation (Baxter et al., Signal transduction mediated by the truncated trkB receptor isoforms, trkB.T1 and trkB.T2, *J. Neurosci.* 17:2683–2690 (1997); Hapner et al., Neural differentiation promoted by truncated trkC receptors in collaboration with p75(NTR), *Dev. Biol.* 201:90–100 (1998); Haapasoalo et al., Expression of the naturally occurring truncated trkB neurotrophin receptor induces outgrowth of filopodia and processes in neuroblastoma cells, *Oncogene* 18:1285–1296 (1999)), truncated trk receptors are generally thought to inhibit trk-mediated neurotrophin signaling by interacting with full-length receptors to form inactive heterodimers (Eide et al., Neurotrophins and their receptors-current concepts and implications for neurological disease, *Exp. Neurol.* 121:200–214 (1996)). The expression of truncated trk receptors is developmentally regulated (Fryer et al., Developmental and mature expression of full-length and truncated trkB receptors in the rat forebrain, *J. Comp. Neurol.* 374:21–40 (1996)) and may represent a normal mechanism for modulating the cellular response to specific neurotrophins (Ninkina et al., Expression and function of TrkB variants in developing sensory neurons, *EMBO J.* 15:6385–6393 (1996)).

The trisomy 16 (Ts16) mouse has a triplication of chromosome 16 (Coyle et al., Down syndrome, Alzheimer's disease and the trisomy 16 mouse, *Trends Neurosci.* 11:390–394 (1988)). A cassette of approximately 185 genes on human chromosome 21 is located on mouse chromosome 16 (Hattori et al., The chromosome 21 mapping and sequencing consortium (2000) The DNA sequence of human chromosome 21, *Nature* 405:311–319 (2000)). As such Ts16 mice share a common genetic defect with the human disorder, Down syndrome (trisomy 21; DS) even though some mouse chromosome 16 genes that are not on human chromosome 21 are overexpressed in Ts16 mice. DS is characterized by mental retardation and, in patients over 40 years of age, Alzheimer's disease (AD) (Mann et al., Alzheimer's presenile dementia, senile dementia of Alzheimer type and Down's syndrome in middle age form an age related continuum of pathological changes, *Neuropathol. Appl. Neurobiol.* 10:185–207 (1984)). Neurons from embryonic Ts16 mice undergo accelerated death by apoptosis (Bambrick et al., Glutamate as a hippocampal neuron survival factor: an inherited defect in the trisomy 16 mouse, *Proc. Natl. Acad.*

*Sci. USA* 92:9692–9696 (1995); Stabel-Burow et al., Glutathione levels and nerve cell loss in hippocampal cultures from trisomy 16 mouse—a model of Down syndrome, *Brain Res.* 765:313–318 (1997); Hallam and Maroun, Anti-gamma interferon can prevent the premature death of trisomy 16 mouse cortical neurons in culture, *Neurosci. Lett.* 252:17–20 (1998); Bambrick and Krueger, Neuronal apoptosis in mouse trisomy 16: mediation by caspases, *J. Neurochem.* 72:1769–1772 (1999)), as do cultured cortical neurons from DS fetuses (Busciglio and Yankner, Apoptosis and increased generation of reactive oxygen species in Down's syndrome neurons in vitro, *Nature* 378:776–779 (1995)). CNS neurons produce BDNF in response to excitatory stimuli. This endogenously produced BDNF mediates activity-dependent neuron survival (Ghosh et al., Requirement for BDNF in activity-dependent survival of cortical neurons, *Science* 263: 1618–1623 (1994)) However, Ts16 hippocampal neurons do not exhibit activity-dependent survival (Bambrick et al., Glutamate as a hippocampal neuron survival factor: an inherited defect in the trisomy 16 mouse, *Proc. Natl. Acad. Sci. USA* 92:9692–9696 (1995)). It is possible that the accelerated death of Ts16 neurons results from failure of BDNF signaling.

This invention demonstrates that Ts16 neurons fail to respond to BDNF. This failure accounts for their accelerated death and results from altered expression of a trkB isoform.

BRIEF DESCRIPTION OF THE INVENTION

It is an object of this invention to treat or prevent neuro-degenerative disorders or neuro-developmental disorders by increasing the amount of full-length TrkB polypeptide in neurons. It is a further object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by increasing the amount of full-length TrkB polypeptide in neurons. It is a further object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by increasing the amount of full-length TrkB polypeptide in neurons and by administering neurotrophins. It is another object of this invention that, in order to increase the amount of full-length TrkB polypeptide in neurons, one can administer nucleic acids which encode for full-length TrkB polypeptide or that one can administer full-length TrkB polypeptides.

It is an object of this invention to treat or prevent neuro-degenerative disorders or neuro-developmental disorders by decreasing the amount of truncated TrkB polypeptides in neurons. It is a further object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by decreasing the amount of truncated TrkB polypeptides in neurons. It is also an object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by decreasing the amount of truncated TrkB polypeptides in neurons and by administering neurotrophins. It is a further object of this invention that one can decrease the amount of truncated TrkB polypeptides in neurons by administering nucleic acids which encode anti-sense RNA specific for truncated TrkB polypeptides or by administering nucleic acids which encode for double stranded RNA specific for truncated TrkB polypeptides.

It is an object of this invention to treat or prevent neuro-degenerative disorders or neuro-developmental disorders by increasing the ratio of the amount of full-length TrkB polypeptide to the amount of truncated TrkB polypeptides. It is a further object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by increasing the ratio of the amount of full-length TrkB polypeptide to the amount of truncated TrkB polypeptides. It is also an object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by increasing the ratio of the amount of full-length TrkB polypeptide to the amount of truncated TrkB polypeptides in neurons and by administering neurotrophins. It is a further object of this invention that one can increase the ratio of the amount of full-length TrkB polypeptide to the amount of truncated TrkB polypeptides by administering nucleic acids or polypeptides which encode for full-length TrkB polypeptide or by administering nucleic acids which encode for anti-sense RNA specific for truncated TrkB polypeptides or by administering nucleic acids which encode for double stranded RNA specific for truncated TrkB polypeptides, or by administering a combination thereof.

It is an object of this invention to treat or prevent neuro-degenerative disorders or neuro-developmental disorders by increasing the amount of full-length TrkC polypeptide in neurons. It is a further object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by increasing the amount of full-length TrkC polypeptide in neurons. It is a further object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by increasing the amount of full-length TrkC polypeptide in neurons and by administering neurotrophins. It is another object of this invention that, in order to increase the amount of full-length TrkC polypeptide in neurons, one can administer nucleic acids which encode for full-length TrkB polypeptide or that one can administer full-length TrkC polypeptides.

It is an object of this invention to treat or prevent neuro-degenerative disorders or neuro-developmental disorders by decreasing the amount of truncated TrkC polypeptides in neurons. It is a further object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by decreasing the amount of truncated TrkC polypeptides in neurons. It is also an object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by decreasing the amount of truncated TrkC polypeptides in neurons and by administering neurotrophins. It is a further object of this invention that one can decrease the amount of truncated TrkC polypeptides in neurons by administering nucleic acids which encode for anti-sense RNA specific for truncated TrkC polypeptides or by administering nucleic acids which encode for double stranded RNA specific for truncated TrkC polypeptides.

It is an object of this invention to treat or prevent neuro-degenerative disorders or neuro-developmental disorders by increasing the ratio of the amount of full-length TrkC polypeptide to the amount of truncated TrkC polypeptides. It is a further object of this invention to treat or prevent Alzheimer's disease, Parkinson's disease, Huntington's disease, amyotrophic lateral sclerosis (Lou Gehrig's disease), the adverse neurologic complications of Down syndrome, diabetic peripheral neuropathy, other types of peripheral neuropathy, and neuron death resulting from injury such as stroke, cerebral ischemia, or chemical and/or physical trauma to the central or peripheral nervous system by increasing the ratio of the amount of full-length TrkC polypeptide to the amount of truncated TrkC polypeptides. It is a further object of this invention that one can increase the ratio of the amount of full-length TrkC polypeptide to the amount of truncated TrkC polypeptides by administering nucleic acids which encode for full-length TrkC polypeptide or by administering nucleic acids which encode for anti-sense RNA specific for truncated TrkC polypeptides or by administering nucleic acids which encode for double stranded RNA specific for truncated TrkC polypeptides, or by administering a combination thereof.

It is also an object of this invention to inhibit the progression of a neuro-degenerative disorder or a neuro-developmental disorder in a mammal by administering a vector containing nucleic acids to alter the ratio of the amount of full-length TrkB polypeptide to the amount of truncated TrkB polypeptides in a neuron. It is a further object of this invention that the vector contain isolated nucleic acid encoding (a) full-length TrkB polypeptide, (b) anti-sense RNA specific for truncated TrkB polypeptides, (c) double stranded RNA specific for truncated TrkB polypeptides, or (d) a combination thereof. It is another object of this invention that the vector be a plasmid or a virus, and if a virus, be selected from a group consisting of herpesvirus, adenovirus, adeno associated virus, retrovirus, vaccinia virus, and canary pox virus.

It is another an object of this invention to inhibit the progression of a neuro-degenerative disorder or a neuro-developmental disorder in a mammal by administering a vector containing nucleic acids to alter the ratio of the amount of full-length TrkC polypeptide to the amount of truncated TrkC polypeptides in a neuron. It is a further object of this invention that the vector contain isolated nucleic acid encoding for (a) full-length TrkC polypeptide, (b) anti-sense RNA specific for truncated TrkC polypeptides, (c) double stranded RNA specific for truncated TrkC polypeptides, or (d) a combination thereof. It is another object of this invention that the vector be a plasmid or a virus, and if a virus, be selected from a group consisting of herpesvirus, adenovirus, adeno associated virus, retrovirus, vaccinia virus, and canary pox virus.

It is an object of this invention to treat a disease characterized by an increased ratio of the amount of truncated TrkB polypeptides to the amount of full-length TrkB polypeptides in a cell as compared to the ratio of these polypeptides in a normal, healthy mammal by administering a vector containing nucleic acids to alter the ratio of the amount of truncated TrkB polypeptides to the amount of full-length TrkB polypeptide in a cell. It is a further object of this invention that the vector contain isolated nucleic acid encoding for (a) full-length TrkB polypeptide, (b) anti-sense RNA specific for truncated TrkB polypeptides, (c) double stranded RNA specific for truncated TrkB polypeptides, or (d) a combination thereof. It is another object of this invention that the vector be a plasmid or a virus, and if a virus be selected from a group consisting of herpesvirus, adenovirus, adeno associated virus, retrovirus, vaccinia virus, and canary pox virus.

It is an object of this invention to treat a disease characterized by an increased ratio of the amount of truncated TrkC polypeptides to the amount of full-length TrkC polypeptides in a cell as compared to the ratio of these polypeptides in a normal, healthy mammal by administering a vector containing nucleic acids to alter the ratio of the amount of truncated TrkC polypeptides to the amount of full-length TrkC polypeptide in a cell. It is a further object of this invention that the vector contain isolated nucleic acid encoding for (a) full-length TrkC polypeptide, (b) anti-sense RNA specific for truncated TrkC polypeptides, (c) double stranded RNA specific for truncated TrkC polypeptides, or (d) a combination thereof. It is another object of this invention that the vector be a plasmid or a virus, and if a virus be selected from a group consisting of herpesvirus, adenovirus, adeno associated virus, retrovirus, vaccinia virus, and canary pox virus.

It is another object of this invention to inhibit the progression of a neuro-degenerative disorder or a neuro-developmental disorder in an animal by administering (a) a polypeptide for full-length TrkB, or a mutant, variant, homolog, or fragment thereof having the same activity as full-length TrkB, (b) a polypeptide for full-length TrkC, or a mutant, variant, homolog, or fragment thereof having the same activity as full-length TrkC, (c) a nucleic acid encoding for full-length TrkB, or a mutant, variant, homolog, or fragment thereof having the same activity as full-length TrkB, (d) a nucleic acid encoding for full-length TrkC, or a mutant, variant, homolog, or fragment thereof having the same activity as full-length TrkC, or (e) a combination of the above.

It is an object of this invention to treat or prevent neuro-degenerative disorders or neuro-developmental disorders by administering exogenous polynucleotides which encode full-length TrkB polypeptide to increase the expression of full-length TrkB polypeptide. It is a further object of this invention to administer neurotrophins in combination with the administered exogenous polynucleotides which encode for full-length TrkB polypeptide. It is a further object of this invention that the neuro-degenerative disorders or neuro-developmental disorders Alzheimer's disease, Parkinson's disease, Huntington's disease, amyotrophic lateral sclerosis (Lou Gehrig's disease), the adverse neurologic complications of Down syndrome, diabetic peripheral neuropathy, and other types of peripheral neuropathy. It is also an object of this invention that neuro-degenerative disorders or neuro-developmental disorders can include neuron death resulting from an injury such as a stroke, cerebral ischemia, or chemical and/or physical trauma; to the central or peripheral nervous system.

It is an object of this invention to treat or prevent neuro-degenerative disorders or neuro-developmental disorders by administering exogenous polynucleotides to decrease the expression of truncated TrkB polypeptides. It is a further object of this invention to administer neurotrophins in combination with the administered exogenous polynucleotides. It is also an object of this invention that the exogenous polynucleotides encode for anti-sense RNA or double stranded RNA for truncated trkB. It is a further object of this invention that the neuro-degenerative disorders or neuro-developmental disorders Alzheimer's disease, Parkinson's disease, Huntington's disease, amyotrophic lateral sclerosis (Lou Gehrig's disease), the adverse neurologic complications of Down syndrome, diabetic peripheral neuropathy, and other types of peripheral neuropathy. It is also an object of this invention that neuro-degenerative disorders or neuro-developmental disorders can include neuron death resulting from an injury such as a stroke, cerebral ischemia, or chemical and/or physical trauma; to the central or peripheral nervous system.

It is an object of this invention to treat or prevent neuro-degenerative disorders or neuro-developmental disorders by administering exogenous polynucleotides which encode for full-length TrkC polypeptide to increase the expression of full-length TrkC polypeptide. It is a further object of this invention to administer neurotrophins in combination with the administered exogenous polynucleotides which encode for full-length TrkC polypeptide. It is a further object of this invention that the neuro-degenerative disorders or neuro-developmental disorders Alzheimer's disease, Parkinson's disease, Huntington's disease, amyotrophic lateral sclerosis (Lou Gehrig's disease), the adverse neurologic complications of Down syndrome, diabetic peripheral neuropathy, and other types of peripheral neuropathy. It is also an object of this invention that neuro-degenerative disorders or neuro-developmental disorders can include neuron death resulting from an injury such as a stroke, cerebral ischemia, or chemical and/or physical trauma; to the central or peripheral nervous system.

It is an object of this invention to treat or prevent neuro-degenerative disorders or neuro-developmental disorders by administering exogenous polynucleotides to decrease the expression of truncated TrkC polypeptides. It is a further object of this invention to administer neurotrophins in combination with the administered exogenous polynucleotides. It is also an object of this invention that the exogenous polynucleotides encode for anti-sense RNA or double stranded RNA for truncated trkC. It is a further object of this invention that the neuro-degenerative disorders or neuro-developmental disorders Alzheimer's disease, Parkinson's disease, Huntington's disease, amyotrophic lateral sclerosis (Lou Gehrig's disease), the adverse neurologic complications of Down syndrome, diabetic peripheral neuropathy, and other types of peripheral neuropathy. It is also an object of this invention that neuro-degenerative disorders or neuro-developmental disorders can include neuron death resulting from an injury such as a stroke, cerebral ischemia, or chemical and/or physical trauma; to the central or peripheral nervous system.

It is an object of this invention to have a pharmaceutical composition containing a vector having nucleic acids encoding for full-length TrkB polypeptide; and a pharmaceutically acceptable carrier.

It is another object of this invention to have a pharmaceutical composition containing a vector having nucleic acids encoding for full-length TrkC polypeptide; and a pharmaceutically acceptable carrier.

It is another object of this invention to have a pharmaceutical composition containing a vector having nucleic acids encoding for anti-sense RNA or double stranded RNA for a truncated TrkB isoform; and a pharmaceutically acceptable carrier.

It is another object of this invention to have a pharmaceutical composition containing a vector having nucleic acids encoding for anti-sense RNA or double stranded RNA for a truncated TrkC isoform; and a pharmaceutically acceptable carrier.

DETAILED DESCRIPTION OF THE INVENTION

Figure 1A:
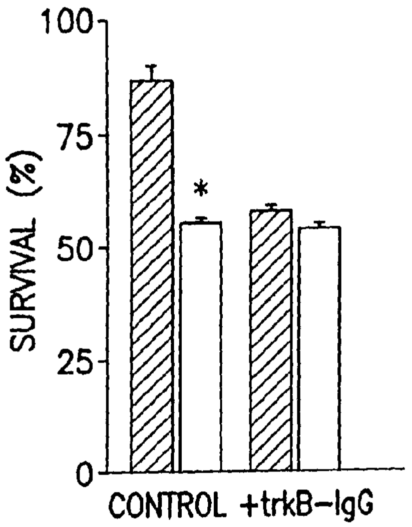
FIG. 1A illustrates the survival of euploid (filled bars) and Ts16 (open bars) hippocampal neurons at 5.5 days in vitro in the continuous presence of B27.

This invention involves using gene therapy to treat or prevent neuro-degenerative disorders and developmental disorders such as Alzheimer's disease (AD), Parkinson's disease (PD), Huntington's disease (HD), amyotrophic lateral sclerosis (Lou Gehrig's disease) (ALS) and the adverse neurologic complications of Down syndrome (DS). For the purposes of this invention, neuro-degenerative disorders and developmental disorders can include neural apoptosis or death resulting from injury where the injury can include, but not be limited to, stroke, cerebral ischemia, or chemical and/or physical trauma to the central or peripheral nervous system. Furthermore, this invention involves using nucleic acids encoding the full-length isoforms of TrkB and TrkC, the truncated isoforms of TrkB and TrkC, anti-sense RNA against the full length and truncated isoforms TrkB, and anti-sense RNA against the full-length and truncated isoforms of TrkC to treat or prevent neuro-degenerative disorders and developmental disorders. One utilizes these nucleic acids to preferentially express in a desired cell a desired nucleic acid or a desired nucleic acid and its encoded polypeptide to alter the level of endogenous expression of the isoforms of TrkB and/or the isoforms of TrkC. This invention also involves using polypeptides for full length TrkB and/or full length TrkC to treat or prevent neuro-degenerative disorders and developmental disorders. One can alter the ratio of the amount of truncated TrkB to full length TrkB in a cell, or the ratio of the amount of truncated TrkC to full length TrkC, or the ratio of full length TrkB to truncated TrkC, or the ratio of full length TrkC to truncated TrkB in a cell to order to treat or prevent the above mentioned neuro-degenerative disorders and developmental disorders.

In addition, this invention involves using nucleic acids encoding the full-length isoforms of TrkB and TrkC, the truncated isoforms of TrkB and TrkC, anti-sense RNA against the full length and truncated isoforms TrkB, and anti-sense RNA against the full-length and truncated isoforms of TrkC to selectively induce neural apoptosis.

Increasing the level of expression of full-length TrkB polypeptide or decreasing the level of expression of truncated TrkB polypeptide is shown herein to protect Ts16 hippocampal neurons from death when exposed to BDNF. Furthermore, increasing the level of expression of full-length TrkB polypeptide or decreasing the level of expression of truncated TrkB polypeptide in mouse Ts16 neurons, a naturally occurring model for DS, resulted in a slower rate of apoptosis when the neurons are exposed to BDNF, demonstrating the anti-apoptotic activity of alterations of the level of expression of the truncated and full-length versions of TrkB specifically with respect to genetic defects associated with neurodegeneration. Given that many clinically-significant neuro-degenerative disorders are characterized by neuronal apoptosis, the invention makes use of the anti-apoptotic activity of altered levels of expression of truncated and full-length TrkB polypeptides to treat such disorders, including, but not limited to, AD, ALS, DS, PD, and HD. The data presented herein demonstrate the usefulness of altering the levels of expression of full-length and truncated TrkB polypeptides in inhibiting neuronal apoptosis, including that associated with neuro-degenerative disorders.

The invention includes a method of inhibiting apoptosis of neuronal cells in a mammal. The method comprises administering to the mammal an apoptosis-inhibiting amount of an isolated nucleic acids encoding full-length TrkB, anti-sense RNA specific for one or more isoforms of truncated TrkB, double-stranded RNA specific for one or more isoforms of truncated TrkB, full-length TrkC, anti-sense RNA specific for one or more isoforms of truncated TrkC, and/or double-stranded RNA specific for one or more isoforms of truncated TrkC.

For this invention, the amino acid and nucleotide sequences of the human full-length TrkB, human truncated TrkB isoforms (for example, TrkB.T1 and TrkB.Shc), mouse full-length TrkB, and mouse truncated TrkB isoforms (for example, TrkB.T1) are useful. Also useful for this invention are the amino acid and nucleotide sequences of the human full-length TrkC, human truncated TrkC isoforms, mouse full-length TrkC, and mouse truncated TrkC isoforms.

The human full-length TrkB nucleotide sequence (SEQ ID NO: 1) and amino acid sequence (SEQ ID NO: 2) are found at GenBank accession number NM_006180. Recently, it was reported that there are multiple distinct isoforms of truncated TrkB (Stoilov P, et al., Analysis of the Human TrkB Gene Genomic Organization Reveals Novel TrkB Isoforms, Unusual Gene Length, and Splicing Mechanism, *Biochem. Biophys. Res. Commun.,* 290(3):1054–1065 (2002)). One isoform is a homolog of the mouse truncated TrkB.T1 and the other isoform, designated TrkB.Shc. TrkB-.Shc contains a tyrosine that binds to the downstream effector, shc, but lacks kinase activity. In fact, it has been report that there are at least two isoforms of the human TrkB.Shc. The nucleotide sequence (SEQ ID NO: 3) and the amino acid sequence (SEQ ID NO: 4) for the human homolog of mouse TrkB.T1 are found at GenBank accession number S76474. The nucleotide sequence (SEQ ID NO: 5) and the amino acid sequence (SEQ ID NO: 6) for one isoform of human TrkB.Shc are found at GenBank accession number AF410900. The nucleotide sequence (SEQ ID NO: 7) and the amino acid sequence (SEQ ID NO: 8) for the other isoform of human TrkB.Shc are found at GenBank accession number AF410901.

The nucleotide sequence (SEQ ID NO: 9) and amino acid sequence (SEQ ID NO: 10) for the mouse full-length TrkB (TrkB.FL) are found at GenBank accession number X17647. The nucleotide sequence (SEQ ID NO: 11) and amino acid sequence (SEQ ID NO: 12) for the mouse truncated TrkB (TrkB.T1) are found at GenBank accession number M33385.

The human full-length TrkC nucleotide sequence (SEQ ID NO: 13) and amino acid sequence (SEQ ID NO: 14) are found at GenBank accession number XM_038336. Human truncated TrkC nucleotide sequences for two exons (exons 13B and 14B) which are specific for this protein are listed with GenBank. The nucleotide sequence for exon 13B (SEQ ID NO: 15) is found at GenBank accession numbers AJ224536 and the nucleotide sequence for exon 14B (SEQ ID NO: 16) is found at GenBank accession numbers AJ224537.

It appears that there are two isoforms of truncated mouse TrkC (isoform 1 and isoform 2). For isoform 1 of mouse truncated TrkC, the nucleotide and amino acid sequences are found at GenBank accession number AF035399. For isoform 2 of mouse truncated TrkC, the nucleotide and amino acid sequences are found at GenBank accession number AF035400.

Also useful to the invention is an isolated full-length TrkB polypeptide or a mutant, variant, homolog, or fragment thereof having the activity of full-length TrkB, as described herein.

Useful to the invention is an isolated full-length TrkC polypeptide or a mutant, variant, homolog, or fragment thereof having the activity of full-length TrkC, as described herein.

Also useful in this invention is anti-sense RNA specific for the various proteins of this invention (e.g., isoforms of truncated TrkB, isoforms of truncated TrkC, full-length TrkB, and full-length TrkC) and polynucleotides which encode the anti-sense RNA. Anti-sense RNA can range in size from 10 through 100, more preferably from 18 through 30, nucleotides long, if the anti-sense RNA is being administered directly to a cell. If, however, the anti-sense RNA is to generated inside a cell using a vector, the coding sequences for the anti-sense RNA can range from 20 to several thousand nucleotides in length.

One example the anti-sense RNA specific for mouse truncated TrkB.T1 is the 1089 base pair sequence in SEQ ID NO: 17. Another example of anti-sense RNA sequence useful for reducing the amount of mouse truncated TrkB in a cell is AAGCAGGCUG CAGACAUCCU (SEQ ID NO: 18). An example of anti-sense RNA useful for reducing the amount of human truncated TrkB.T1 in a cell is provided in SEQ ID NO: 19. An example of anti-sense RNA useful for reducing the amount of human truncated TrkB.Shc in a cell is provided in SEQ ID NO: 20; this sequence is directed at exon 19 which appears to be conserved among the isoforms of TrkB.Shc. For all anti-sense RNA sequences, one can replace thymine with uracil or replace uracil with thymine.

Two examples of anti-sense RNA specific for human truncated TrkC are provided. One sequence (SEQ ID NO: 21) is specific for exon 13B; the other sequence (SEQ ID NO: 22) is specific for exon 14B. Alternatively, one can use both sequences in tandem to generate an anti-sense RNA specific for exons 13B and 14B of human truncated TrkC.

Double-stranded RNA specific for the various proteins of this invention (e.g., isoforms of truncated TrkB, isoforms of truncated TrkC, full-length TrkB, and full-length TrkC) and polynucleotides which encode the double-stranded RNA are also useful in this invention. With double-stranded RNA, one can generate double-stranded RNA having lengths of 10, 15, 20, 25, 30, 35, 40, 45, 50, or more base pairs. It is preferable that these double-stranded RNA are specific for the unique sequences for the gene for which one is trying to inhibit transcription or translation. For human TrkB.T1, one can use double-stranded RNA for any of the sequences listed in SEQ ID NO: 19; for human TrkB.Shc, use sequences in SEQ ID NO: 20; for human TrkC use sequences in SEQ ID NO: 21 or SEQ ID NO: 22.

A number of TrkB and TrkC encoding nucleic acid combinations are useful in the invention. For example, an isolated nucleic acid encoding full-length TrkB may be delivered to a neuron in combination with an isolated nucleic acid encoding full-length TrkC. In another example, anti-sense RNA specific for one or more isoforms of truncated TrkB and for one or more isoforms of truncated TrkC may be delivered to a neuron in combination with each other. Another example of a combination is nucleic acids encoded for full-length TrkB and for anti-sense RNA specific for one or more isoforms of truncated TrkC. Yet another example is anti-sense RNA specific for one or more isoforms of truncated TrkB and full-length TrkC. Also covered by this invention is the combination of polynucleotides encoding full-length TrkB and anti-sense RNA specific for one or more isoforms of truncated TrkB. Also covered is the combination of polynucleotides encoding full-length TrkC and anti-sense RNA specific for one or more isoforms of truncated TrkC. These combination nucleic acids can be linked using standard molecular biology techniques and delivered as a single fused nucleic acid molecule, or they may be present in distinct and separate plasmids or vectors, or the nucleic acids may be on one plasmid or vector but under the control of different promoters. The nucleic acids can be polycistronic under one promoter, or they can be expressed independently using different promoters. Further, fragments of either molecule may be delivered, wherein each fragment retains biological activity of the respective protein encoded thereby.

Modes of Administration

The isolated nucleic acid encoding full length TrkB or the isolated nucleic acid encoding for anti-sense truncated TrkB can be administered to a mammal using a variety of methods. In a preferred embodiment of the invention, trkB polynucleotides are delivered using a vector. Numerous vectors are known in the art including, but not limited to, linear polynucleotides, polynucleotides associated with ionic or amphiphilic compounds, plasmids, and viruses. Thus, the term “vector” includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, herpesvirus vectors, adenoviral vectors, adeno-associated virus vectors, retroviral vectors, and the like.

Useful in the invention is a vector comprising the nucleic acid encoding TrkB (either anti-sense truncated or sense full length isoform). Also useful is a vector comprising the nucleic acid encoding for TrkC (either anti-sense truncated or sense full length isoform). The nucleic acids may be present within separate vectors or within the same vector. When the nucleic acids are within the same vector, the nucleic acids may be polycistronic such that their expression is linked to one another or they may be expressed independently from one another. Many vectors may be useful for delivering the combination of TrkB and TrkC to cells in a mammal.

Given the neurotropism of Herpes Simplex Virus 2 (HSV-2), this virus serves as a useful vector for delivery of polynucleotides encoding TrkB and/or TrkC (full-length and truncated isoforms) and polynucleotides encoding anti-sense RNA and double-stranded RNA specific for TrkB and/or TrkC(full-length and truncated isoforms) to neurons. Particularly useful in the invention, is an HSV-2 vector wherein the RR domain of ICP10 in HSV-2 have been deleted (ICP10deltaRR), thereby rendering the virus replication-defective but retaining the anti-apoptotic activity of the PK domain of ICP10. Alternatively, one can use a HSV-2 vector where both the RR and PK domains in HSV-2 have been deleted (ICP10deltaPK,RR). Other viral and non-viral vectors containing the desired polynucleotides of this invention may also be useful in the invention. For example, retrovirus vectors containing the desired polynucleotides can be used to stably infect neuronal stem cells useful in ex-vivo gene therapy. Other viral vectors including, but not limited to, adenovirus, vaccinia virus, canary pox virus, and adeno associated virus are useful for this invention.

Vectors containing the desired polynucleotides can be constructed by standard molecular biology techniques. An HSV-2 vector, ICP10deltaRR, wherein the RR domain of ICP10 was replaced with a nucleic acid encoding LacZ was constructed previously (U.S. Pat. Nos. 6,013,265, 6,054,131, and 6,207,168). The addition of polynucleotides encoding for TrkB and/or TrkC isoforms (full-length and truncated), anti-sense RNA specific for TrkB and/or TrkC isoforms (full-length and truncated), and/or double-stranded RNA specific for TrkB and/or TrkC isoforms (full-length and truncated) to this HSV-2 vector can be accomplished using well-known in the art-field techniques. Other HSV-2 vectors encoding the desired polynucleotides of this invention can be constructed by similar methods.

Also useful in the invention is having the desired polynucleotide sequences operably linked to a promoter regulatory sequence that facilitates expression of the desired polynucleotide sequences. Tissue specific and/or inducible promoters particularly useful for this invention. Because the invention relates to the expression of the desired polynucleotide sequences in neuronal cells, the following neuron-specific promoters will be particularly useful: neuron-specific enolase (NSE) and tyrosine hydroxylase (TH) promoters, TH-NFH (neurofilament heavy subunit) chimeric promoter, and the golli promoter (each of these promoters is described in detail below). Endogenous mammalian NSE is expressed in essentially all neurons, beginning during development at the time of synaptogenesis; its activity increases at a steady rate into adulthood when amounts of this protein can reach levels of up to 1% of the total cell protein (Marangos, et al., Neuron specific enolase, a clinically useful marker for neurons and neuroendocrine cells, *Ann. Rev. Neurosci.* 60:269–295 (1987)). The pattern of expression of this promoter makes it a good candidate for conferring long-term expression of foreign genes on adult neurons following delivery by a viral vector. The TH-NFH promoter supports long-term gene expression in striatal neurons (Wang, et al., General strategy for constructing large HSV-1 plasmid vectors that co-express multiple genes, *Biotechniques* 31:204–212 (2001)). Golli products of the myelin basic protein (MBP) gene have been found to be expressed in neurons during postnatal and embryonic development including Cajal-Retzius and cortical subplate neurons. Moreover, golli expression occurs in other cortical neurons including neurons from cortical layer V and the hippocampus (Pribyl, et al., Expression of the myelin basic protein gene locus in neurons and oligodendrocytes in the human fetal central nervous system, *J. Comp. Neurol.* 374:342–353 (1996); Pribyl, et al., The human myelin basic protein gene is included within a 179-kilobase transcription unit: expression in the immune and central nervous systems, *Proc. Natl. Acad. Sci. USA* 90:10695–10699 (1993)). Consequently, the golli promoter may be useful for driving transgene expression in selected neuronal populations.

Viral promoters including the HSV latency associated transcript (LAT) promoter, the Moloney murine leukemia virus (Mo-MLV) long terminal repeat (LTR), and the human cytomegalovirus (HCMV) immediate early (IE) promoter may also by useful. The LAT promoter includes elements both upstream and downstream of the start site of the minor LAT mRNA from which the intranuclear LATs are derived. Promoter elements referred to as LAP2 (latency active promoter 2) and LAP1 (contains neuronal responsive elements) are independently capable of expressing LAT during viral latency in sensory ganglia. The transgene can be placed downstream of LAP1 near the start of the LAT mRNA or downstream of both promoters within the LAT intron. Stable transgene expression has been achieved in sensory ganglia, but expression in CNS neurons was less vigorous (Fink, et al., Engineering herpes simplex virus vectors for gene transfer to neurons, *Nature Med.* 3:357–359 (1997)). The LTR of Mo-MLV has been used with HSV vectors to yield stable expression of the LacZ gene in sensory neurons and extended expression in motor neurons of the hypoglossal nucleus (Dobson, et al., A latent, nonpathogenic HSV-1-derived vector stably expresses beta-galactosidase in mouse neurons, *Neuron* 5:353–360 (1990)). The HCMV IE promoter is a very strong constitutive promoter that is active in a wide variety of cell types including CNS neurons both in vitro (Johnson, et al., Effects of gene transfer into cultured CNS neurons with a replication-defective herpes simplex virus type 1 vector, *Mol. Brain Res.* 12:95–102 (1992)) and in vivo (Wood, et al., Specific patterns of defective HSV-1 gene transfer in the adult central nervous system: implications for gene targeting, *Exp. Neurol.* 130:127–140 (1994)). The vectors described above may also comprise such promoters operably linked to the desired polynucleotide sequences.

Another useful delivery technique of nucleotides and polypeptides is intracranial injection of the nucleic acids, or of a vector containing the desired nucleic acids, or of the polypeptides. One can also combine polynucleotides with basic polypeptides, such as poly-lysine and poly-histidine, prior to applying and/or injecting the polynucleotides into neurons.

Another useful delivery technique of polynucleotides, including vectors, is electropermeabilization. Electropermeabilization can be used in gene therapy to administer DNA directly to an animal (Drabick, J J, et al., Cutaneous transfection and immune responses to intradermal nucleic acid vaccination are significantly enhanced by in vivo electropermeabilization, *Mol. Ther.,* 3(2):249–55 (2001)). Alternatively, electroporation can be used to get DNA into a cell and then the cell is placed inside the animal. Electroporation is well-known in the art field and can be performed using the following briefly described method: A mixture of 150 ml cells and plasmid DNA are electroporated in a 0.2 cm curettes in a Gene Pulser (BioRad Laboratories, Hercules, Calif.) using 2.5 kV, 200W, 25 mF, or 1.75 kV, 600W, 25 mF. The plasmid DNA can encode anti-sense RNA, double-stranded RNA, and/or full-length or truncated proteins under control of a constitutive or inducible promoter, as described above. Combining the polynucleotides with basic polypeptides, such as poly-lysine and poly-histidine, may be useful prior to electropermeabilization or electroporation.

Synthesized oligonucleotides can be introduced into suitable cells by a variety of means including electroporation, calcium phosphate precipitation, or microinjection. Polynucleotides may also be introduced into cells by using bacteria as carriers (see for example U.S. Pat. No. 6,150,170; and International Patent Application PCT/US98/21093 filed Oct. 7, 1998).

In the methods of the invention, full-length or truncated TrkB isoforms may be delivered to neuronal cells in the form of a nucleic acids encoding full-length or truncated TrkB isoforms, preferably using vectors or liposomes, or it may be delivered to cells in the form of a polypeptide, or a mutant, variant, homolog, or fragment thereof having the activity of full-length or truncated TrkB isoforms using liposomes. Thus, the use of full-length or truncated TrkB isoform polypeptide and fragments thereof, including all mutants and variants having full-length or truncated TrkB isoform biological activity as defined here, are included in the methods of the invention. Full-length or truncated TrkB isoform polypeptides can be easily generated using methods well known in the art described, for example, in Sambrook et al. Molecular Cloning: A Laboratory Manual, Cold Spring Harbor Laboratory, New York (1989) and in Ausubel et al, Current Protocols in Molecular Biology, John Wiley & Sons, New York (1997).

In the methods of the invention, full-length or truncated TrkC isoforms may be delivered to neuronal cells in the form of a nucleic acids encoding full-length or truncated TrkC isoforms, preferably using vectors or liposomes, or it may be delivered to cells in the form of a polypeptide, or a mutant, variant, homolog, or fragment thereof having the activity of full-length or truncated TrkC isoforms using liposomes. Thus, the use of full-length or truncated TrkC isoform polypeptide and fragments thereof, including all mutants and variants having full-length or truncated TrkC isoform biological activity as defined here, are included in the methods of the invention. Full-length or truncated TrkC isoform polypeptides can be easily generated using methods well known in the art described, for example, in Sambrook et al. (supra) and in Ausubel et al (supra).

Analogs

The present invention also provides for a method of inhibiting apoptosis using analogs of proteins or peptides encoded by full-length trkB or full length trkC. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. The invention should be construed to include administration of modified full-length TrkB peptides or full-length TrkC peptides including, but not limited to, peptides modified by glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced is a method of inhibiting apoptosis comprising administration of full-length TrkB peptides or full-length TrkC peptides which have phosphorylated amino acid residues, e.g., phosphotyrosine, phosphoserine, or phosphothreonine.

The invention further includes a method of inhibiting apoptosis by administering full-length TrkB polypeptides or full-length TrkC polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Pharmaceutical Compositions

Pharmaceutical compositions comprising the desired polynucleotide sequences, vectors comprising the same, or peptides encoded thereby, may be formulated and administered to a mammal for inhibition of apoptosis. Such compositions are now described.

The invention encompasses the preparation and use of pharmaceutical compositions comprising a TrkB and/or TrkC compound useful for inhibition of apoptosis as an active ingredient. The invention also encompasses the preparation and use of pharmaceutical compositions comprising polynucleotides encoding anti-sense RNA and/or double-stranded RNA specific for one or more isoforms of truncated TrkB and/or truncated TrkC. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

Pharmaceutical compositions that are useful in the methods of the invention may be prepared, packaged, or sold in formulations suitable for parenteral, topical, pulmonary, intranasal, buccal, ophthalmic, intrathecal, intracranial, or another route of administration.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intracranial injections, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention.

Typically dosages of the compound of the invention which may be administered to an animal, preferably a human, range in amount from 1 microgram to about 100 grams for proteins and peptides, $10^3$ to $10^8$ plaque forming units for viruses, and 1 to 500 micrograms for nucleic acids.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

For example, treatment of AD, a chronic disease, may be performed as follows. A viral vector containing polynucleotides encoding anti-sense RNA specific for one or more human truncated TrkB isoforms (SEQ ID NO: 19 and SEQ ID NO: 20) can be given by intranasal spraying, a non-invasive and widely accepted delivery route, although other routes of administration are possible, such as ocular drops. As stated above, $10^3$ to $10^8$ plaque forming units of the viral vector can be used for infection. Assuming that gene expression does not last more than 20 days, monthly re-exposure will be needed (or at least 10 exposures per year).

To treat an acute disease, the viral vector containing polynucleotides encoding anti-sense RNA specific for one or more human truncated TrkB isoforms (SEQ ID NO: 19 and SEQ ID NO: 20) can be administered as described above. Again assuming that gene expression does not last more than 20 days, re-exposure will only be needed 2 or 3 additional times (4 exposures total).

Examples of acute diseases that could be treated with TrkB and/or TrkC (either full-length, anti-sense RNA, and/or double-stranded RNA specific for a truncated isoform) include stroke, cerebral ischemia, brain trauma, and spinal cord injury. Patients suffering any of these injuries experience neuronal apoptosis and may be treated effectively with TrkB and/or TrkC. These types of injuries require treatment within days of the injury and are excellent candidates for the anti-apoptotic use of TrkB and/or TrkC. Thus, administration of TrkB and/or TrkC is useful in inhibiting apoptosis in both the central nervous system as well as the peripheral nervous system, where it will be particularly effective in cases of spinal cord injury and diabetic neuropathy.

Experiment Methods

For the experiments that are described in detail below, the following methods and reagents are used.

Mouse monoclonal antibody to an extracellular epitope on TrkB [anti-TrkB(out)], which recognizes both full-length TrkB (TrkB.FL) and truncated TrkB (TrkB.T1), was obtained from BD Transduction Laboratories (Lexington, Ky.). Antibodies to the neuron-specific microtubule-associated protein, MAP2ab, and hemagluttin (HA) were obtained from Sigma Chemical Co. (St. Louis, Mo.), and anti-p75 was from Chemicon International Corp (Temecula, Calif.). Rabbit polyclonal antibodies to an intracellular epitope on trkB.FL [TrkB(in)] and to an extracellular epitope on TrkC were provided by Dr. L. Reichardt, UCSF (San Francisco, Calif.). Rabbit polyclonal antibody to an intracellular epitope on the T1 isoform of truncated TrkB [TrkB(T1)] (Yan et al., Immunocytochemical localization of TrkB in the central nervous system of the adult rat, *J. Comp. Neurol.*

378:135–157 (1997)) was obtained from Dr. S. C. Feinstein, UCSB (Santa Barbara, Calif.). Polyclonal antibody specific for phospho-trk was obtained from New England BioLabs (Beverly, Mass.). Appropriate rhodamine-, fluorescein- or peroxidase-conjugated secondary antibodies were obtained from Jackson ImmunoResearch Laboratories Inc. (West Grove, Pa.). BDNF and NT-3 were supplied by Regeneron Pharmaceuticals (Tarrytown, N.Y.); FGF-2 (basic fibroblast growth factor) was obtained from Upstate Biotechnology Inc. (Lake Placid, N.Y.). TrkB-IgG (provided by Regeneron) is a soluble fusion protein consisting of the extracellular, BDNF binding domain of rat trkB coupled to an Fc fragment of human IgG (Croll et al., Co-infusion with a TrkB-Fc receptor body carrier enhances BDNF distribution in the adult rat brain, *Exp. Neurol.* 152:20–33 (1998)), which decreases the free extracellular BDNF concentration and inhibits its effects. TrkA-IgG (Regeneron) had no effect on euploid neuron survival demonstrating that there were no non-specific effects of TrkB-IgG (hippocampal neurons do not respond to NGF [Ip et al., Cultured hippocampal neurons show responses to BDNF, NT-3, and NT-4, but not NGF, *J. Neurosci.* 13:3394–3405 (1993)]).

Preparation and characterization of neuron cultures. Hippocampal neurons were cultured from euploid and Ts16 littermate fetuses on embryonic day 15.5 in minimal essential medium (MEM) supplemented with B27 as described in Bambrick et al., Glutamate as a hippocampal neuron survival factor: an inherited defect in the trisomy 16 mouse, *Proc. Natl. Acad. Sci. USA* 92:9692–9696 (1995). In brief, hippocampi are freed of meninges, digested with trypsin, and dissociated by trituration in MEM 10/10 [MEM with Earle's salts/2 nM glutamine/10% (vol/vol) fetal bovine serum/10% (vol/vol) horse serum/penicillin (100 units/ml)/streptomycin (100 units/ml)]. Cells are plated in 50,000 cells per $cm^2$ on 12-mm glass coverslips photoeteched with a lettered grid of 175 mm×175 mm squares (Eppendorf AG, Hamburg, Germany). The coverslips are pretreated with poly(L-lysine) (Sigma). At 1 day in vitro, the MEM 10/10 is replaced with MEM supplemented with B27. The B27 supplement contains optimized concentrations of neuron survival factors including triiodothyronine, cortisol, transferrin, glutathione, DL-a-tocopherol, and insulin. At 2 days in vitro, the medium is changed to MEM with B27. The cultures are maintained at 37° C. in 95% air/5% $CO_2$. Each coverslip is kept in a separate well; two to four coverslips are used for each condition in each experiment. Neurons are plated at $10^4$ cells per $cm^2$ on 12 mm glass coverslips etched with a lettered grid (Eppendorf A G, Hamburg, Germany) for survival experiments and at $5\times10^5$ cells per 35 mm dish for western blots. Initially, (FIG. 1B) coverslips and dishes are coated with poly L-lysine (Sigma); but are changed to coatings of poly L-lysine (Sigma) and merosin (FIG. 1A, and FIGS. 3C–E) because neurons died about half as fast on merosin/poly L-lysine substrate as compared to poly L-lysine alone, however the relative differences between euploid and Ts16 neuron survival and the effects of neurotrophins are identical on the two substrates. Unless otherwise indicated, cell culture reagents are obtained from GIBCO/BRL (Rockville, Md.).

Measurement of neuron survival. At 3 days in vitro, all live neurons in each of five randomly selected, 175 mm×175 mm fields per coverslip (identified by the etched grid) and at least two coverslips per condition were counted using phase contrast microscopy. Cells that had assumed a globular, pyknotic appearance were scored as dead. Separate studies have confirmed that cells scored as live by phase contrast microscopy exclude trypan blue and are not undergoing DNA fragmentation (TUNEL-negative). Depending on the experiment, survival is expressed as the percentage of cells present at 3 days in vitro that remained at 5.5 days in vitro; or, when B27 was removed at 3 days in vitro and the cultures were treated with neurotrophins or FGF-2, survival is expressed as the percentage of neurons present at the time of B27 withdrawal that remained at the end of the treatment period. The significance of differences between euploid and Ts16 cell counts for each condition was determined by student's t-test.

Western blot analysis. SDS-solubilized cell extracts were incubated at 100° C. for five minutes, fractionated on 4–12% NuPAGE bis-tris gels (Invitrogen Corp., Carlsbad, Calif.) and transferred to a nitrocellulose membrane. After blocking in non-fat dried milk, membranes were incubated for 2–16 hours with primary antibody followed by incubation with appropriate peroxidase-conjugated secondary antibodies and visualized by chemiluminescence (ECL, Amersham Pharmacia Biotech Co., Piscataway, N.J.). Blots were quantified by scanning autoradiographs into NIH Image (v 1.62, NIH) to determine the optical density of each band.

Fluorescence immunocytochemistry (ICC). Cultures were fixed in 4% paraformaldehyde and incubated overnight with primary antibody at 4° C. Incubation with rhodamine- or fluorescein-conjugated secondary antibody was for 1 hour. Fluorescence images were acquired using a conventional microscope equipped with epifluorescence optics (Olympus America Co., Melville, N.Y.) or a confocal microscope (Model LSM410; Carl Zeiss, Jena, Germany).

Replication-deficient recombinant adenoviruses. Adenoviruses were generated as described in Gonzalez et al., Disruption of TrkB-mediated signaling induces disassembly of postsynaptic receptor clusters at neuromuscular junctions, *Neuron* 24:567–583 (1999). In brief, the pAdLink plasmid, containing the cytomegalovirus (CMV) promoter/enhancer, an SV40 polyadenylation sequence, and flanking adenovirus backbone sequences, was modified by inserting multiple cloning sites, an IRES from pLIGns, and green fluorescent protein (GFP) (codon-corrected cDNA; GIBCO-BRL). cDNAs encoding other transgenes were then cloned into this plasmid. Recombinant, replication-defective adenovirus was generated by homologous recombination with the viral Ad5, E1a-deleted dl327 backbone in human embryonic kidney 293 stem cells that are permissive for viral replication. The *Escherichia coli* lacZ gene encoding b-gal and the gene for GFP were cloned into pAdLink, and adenovirus was generated. Ad– encodes lacZ and GFP under control of the CMV promoter and an IRES sequence and serves as a control for nonspecific effects of viral infection and over-expression of exogenous protein. A mouse truncated TrkB.T1 cDNA and mouse full-length TrkB cDNA (TrkB.FL) were epitope tagged at the carboxyl terminus of the protein with hemagluttinin (HA) and these genes and the gene for GFP were cloned into the modified pAdLink plasmid. Purified virus was generated after three rounds of plaque selection by a limiting dilution method in 293 cells. The integrity of the viral genome was examined by Southern blot, and the absence of wild-type Ad5 virus was confirmed by PCR using primers specific to the deleted Ela region. Virus was resuspended in HEPES-buffered saline (HBS [pH 7.8]) 10% glycerol, particle density was measured spectrophotometrically at $OD_{260}$, and pfu was determined by plaque assays on agar overlays using a limiting dilution method. Virus aliquots of $1\times10^{12}$ pfu/ml were stored at −70° C. for <4 months, and viral stocks were stored in liquid $N_2$. The hemagglutinin (HA) sequences at the C-terminus of the TrkB.FL and TrkB.T1 enable detection of the exogenous TrkB proteins, independently of endogenous TrkB proteins. In these vectors, GFP was under the control of the CMV promoter and an IRES sequence to allow translation of a bicistronic message. The adenovirus designated AdTR contains DNA which encodes the mouse truncated TrkB isoform (TrkB.T1) (cDNA gift of Dr. M. Barbacid) (SEQ ID NO: 11). It is noted that AdTR lacks the intracellular tyrosine kinase domain of TrkB. The adenovirus designated AdFL contains DNA which encodes the mouse full-length TrkB (TrkB.FL) (SEQ ID NO: 9). Anti-HA immunostaining is used as an indicator of AdFL and AdTR infection in this study; GFP fluorescence is used to confirm infection by Ad− (75% of neurons were infected). Adenovirus mediated transgene expression and function are evaluated by western blot, ICC, and in a PC12 neurite outgrowth assay as described in Gonzalez et al., (supra). An in vitro assay was used to determine whether virally expressed trkB.T1 could decrease BDNF or NT-4/5 signaling through endogenous, full-length TrkB in a dominant-negative fashion. A stably transfected PC12 cell line that expresses TrkB.FL (PC12-trkB) was used; these cells extend neurites in the presence of BDNF. Cells were plated at low-passage number and maintained in medium with 10% horse serum, 5% fetal bovine serum, penicillin (100 units)/streptomycin (100 mg) at 37° C. in 5% $CO_2$. One day after splitting, cells were infected with AdTR or Ad− ($2\times10^8$ pfu/$10^4$ cells), or vehicle. Three days later, 1–100 ng/ml BDNF, NT-4/5 or NGF was added to the medium for 5 days. Cells that were treated with AdTR did not extend neurites in response to BDNF whereas Ad- or untreated cells produced extensive neurites in response to BDNF. As a positive control to evaluate nonspecific effects of viral infection, neurite extension was examined in another cell line (PC63) which expresses TrkA. These cells were also infected with AdTR and Ad−. Neither virus prevented the ability of NGF to stimulate neurite growth in these cells.

Accelerated Death of Ts16 Neurons Due to Failure of BDNF Signaling

Cultures of normal (euploid) and Ts16 neurons were prepared from embryonic littermate hippocampi and maintained in serum-free medium (MEM) containing the chemically-defined supplement, B27 (Brewer et al., Optimized survival of hippocampal neurons in B27-supplemented Neurobasal, a new serum-free medium combination, *J. Neurosci. Res.* 35:567–576 (1993)). The cultures contained almost exclusively postmitotic neurons.

Both euploid and Ts16 cultures contained >95% MAP2ab-immunoreactive neurons with the remainder being flat cells identified as astrocytes by GFAP ICC. The proportion of glial cells was the same in euploid and Ts16 cultures.

Figure 2B:
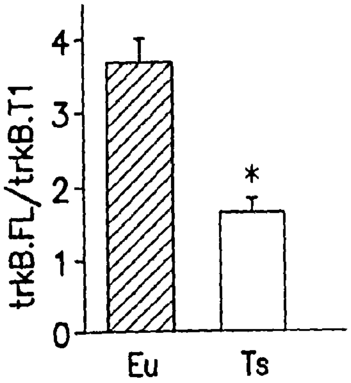
FIG. 2B illustrates the ratio of TrkB.FL to TrkB.T1 in euploid and Ts16 neurons.

Cortical astrocytes, cultured from euploid and Ts16 littermate fetuses as previously described (Bambrick L L, et al., Expression of glial antigens in mouse astrocytes: species differences and regulation in vitro, *J. Neurosci. Res.* 46:305–15 (1996)), contained the same amount of TrkB.T1 by western blot analysis, demonstrating that differences in TrkB.T1 expression (FIGS. 2A, 2B, and 2C) were not due to differences in TrkB.T1 levels in contaminating astrocytes.

By 3 days in vitro, neurons from both genotypes took on the characteristics of differentiated neurons with extensive processes. At this time there were no differences in soma size or in neurite length or branching between the two genotypes. Some cells in both euploid and Ts16 cultures died over 5 days in vitro. Ts16 neurons die about three-times faster than euploid neurons (Bambrick et al., supra (1995); Bambrick and Krueger, Neuronal apoptosis in mouse trisomy 16: mediation by caspases, *J. Neurochem.* 72:1769–1772 (1999)). Similarly, in the present study, about 13% of euploid and about 42% of Ts16 neurons died over a 2.5-day period (FIG. 1A). Addition of TrkB-IgG (2 mg/ml) at 3 days in vitro (Croll et al., supra (1998)) to deplete endogenous BDNF from the medium reduced the survival of euploid neurons to Ts16 levels without affecting Ts16 neuron survival (FIG. 1A). Survival is expressed as % of cells present at 3 days in vitro that were still present at 5.5 days in vitro. This lack of survival demonstrates that BDNF is normally secreted in euploid hippocampal neuron cultures where it promotes neuron survival and that this autocrine BDNF-mediated survival pathway is not functioning in Ts16 cultures.

Figure 1B:
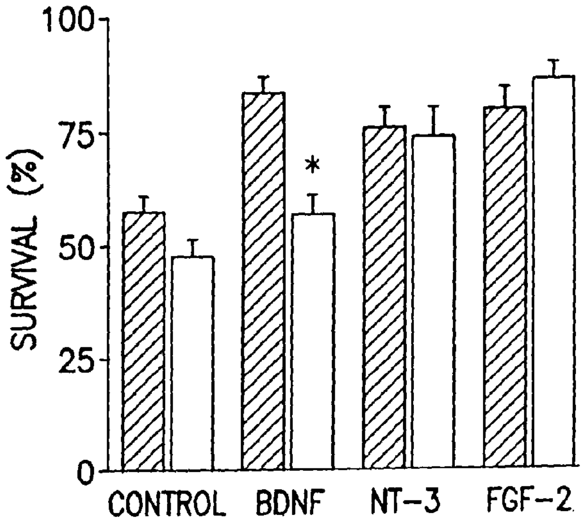
FIG. 1B shows the survival of euploid (filled bars) and Ts16 (open bars) neurons 16 hours after withdrawal of B27 at 3 days in vitro.

In order to determine whether Ts16 neurons were capable of responding to BDNF, B27 was removed at 3 days in vitro and the ability of exogenous BDNF alone to support neuron survival was determined. Removal of B27 caused about half of both euploid and Ts16 neurons to die within one day. In euploid neurons, this death was blocked by BDNF (100 ng/ml) addition at 3 days in vitro (after B27 removal), whereas the Ts16 neurons were not rescued by the exogenous BDNF (FIG. 1B). Survival is expressed as % of cells present at 3 days in vitro that were still present at 4.5 days in vitro. In MEM+BDNF, 16% of euploid neurons and 50% of Ts16 neurons died. Error bars show sem (n=3) and * indicates euploid and Ts16 survival were significantly different by t-test ($p<0.001$). BDNF failed to rescue Ts16 neurons even at 1 mg/ml, ten times the maximally-effective concentration for euploid neurons.

TrkA-IgG had no effect on euploid neuron survival demonstrating that there were no non-specific effects of TrkB-IgG [mouse hippocampal neurons do not respond to NGF (N. Y. Ip, et al, supra (1993))].

To determine whether Ts16 neurons are capable of responding to other survival factors, B27 was withdrawn at 3 days in vitro and replaced with BDNF (100 ng/ml), NT-3 (100 ng/ml), or basic fibroblast growth factor (FGF-2) (10 ng/ml). Survival is determined as % of cells present at the time of B27 withdrawal that were still alive 16 hours later. Survival of euploid neurons in the presence of BDNF, NT-3, and FGF-2 was significantly different ($p<0.05$) from that in the absence of survival factors (vehicle). Survival of Ts16 neurons in the presence of NT-3 and FGF-2, but not in the presence of BDNF, was significantly different ($p<0.05$) from that in the absence of survival factors. Even though BDNF was unable to promote the survival of Ts16 neurons, NT-3 and FGF-2 rescued both euploid and Ts16 neurons to the same extent. Thus, Ts16 neurons have a selective failure of the survival response to BDNF.

Ts16 Neurons Overexpress Truncated trkB

Figure 2A:
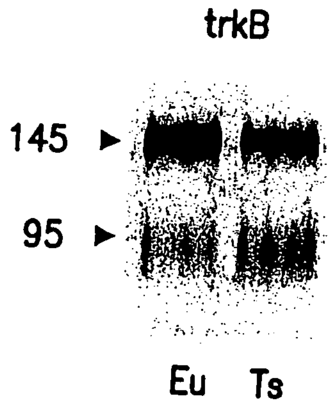
FIG. 2A shows the abnormal expression of TrkB isoforms in Ts16 neurons (Ts) and normal (eu) neurons via western blot, where the full-length isoform is at 145 and the truncated isoform is at 95.
Figure 2C:
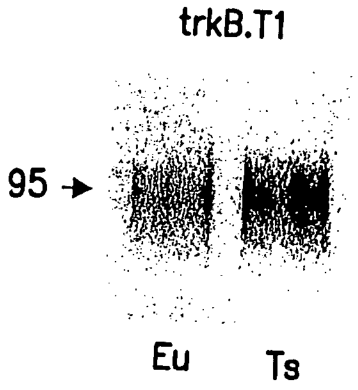
FIG. 2C illustrates a western blot of euploid neurons (eu) and Ts16 neurons (Ts) using anti-TrkB(T1) which labels an internal epitope on TrkB.T1. The band appears at 95.

In order to determine whether Ts16 neurons lack the BDNF receptor, TrkB, the TrkB composition of euploid and Ts16 cultures was analyzed by western blotting with an antibody [anti-TrkB(out)] that recognizes the extracellular domain of the receptor (FIG. 2A). FIG. 2A shows the western blot of euploid and Ts16 hippocampal neurons using anti-TrkB(out), which binds to a common epitope on the extracellular side of full length (145 kDa) and truncated (95 kDa) TrkB. The western blot was performed as described above. Rabbit polyclonal antibodies to an intracellular epitope on TrkB.FL [TrkB(in)] and to an extracellular epitope on TrkC were used as well as rabbit polyclonal antibody to an intracellular epitope on TrkB.T1.

Figure 2E:
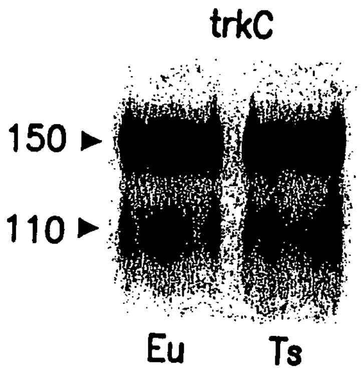
FIG. 2E shows a western blot of euploid neurons (eu) and Ts16 neurons (Ts) using an antibody to TrkC that labels both the full length isoform (150 kDa) and the truncated isoform (110 kDa).
Figure 2D:
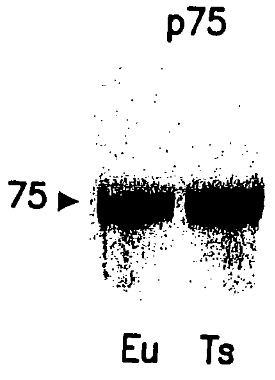
FIG. 2D shows a western blot of euploid neurons (eu) and Ts16 neurons (Ts) using anti-p75, having a band at 75.

In FIG. 2A, euploid and Ts16 neurons expressed both the full-length, functionally active isoform, TrkB.FL (145 kDa) (full-length TrkB) and the catalytically inactive, truncated isoform, TrkB.T1 (95 kDa) (truncated TrkB), which has been proposed to inhibit BDNF signaling via TrkB by a dominant-negative mechanism (Middlemas et al., supra (1991); Eide et al., supra (1996)). Although Ts16 neurons expressed slightly less TrkB.FL, they expressed substantially more TrkB.T1. The ratio of TrkB.FL to TrkB.T1 expresssion was 3.8 in euploid neurons and only 1.5 in Ts16 neurons (see FIG. 2B where the error bars show sem (n=3; *, $p<0.05$)). Overexpression of TrkB.T1 was confirmed using an antibody (Fryer R H, et al., Developmental and mature expression of full-length and truncated trkB receptors in the rat forebrain, *J. Comp. Neurol.* 374:21–40 (1996)) to the unique, intracellular domain of the T1 isoform of TrkB.T1 (see FIG. 2C in which anti-TrkB(T1) was used to label an internal epitope on TrkB.T1). The neurotrophins also bind to the low-affinity neurotrophin receptor, p75, which may modulate neurotrophin-mediated neuron survival in the absence of trk receptors (Casaccia-Bonnefil, P, et al., Neurotrophins: the biological paradox of survival factors eliciting apoptosis, *Cell Death Differ.* 5:357–364 (1998)), however, p75 expression was the same in euploid and Ts16 neurons (FIG. 2D). In addition, the expression of the NT-3 receptor, TrkC, and its truncated isoforms was the same in euploid and Ts16 neurons (FIG. 2E which shows a western blot of euploid and Ts16 neurons using an antibody to TrkC that labels both full length (150 kDa) and truncated (110 kDa) isoforms), consistent with the survival-promoting effect of NT-3 in both genotypes (FIG. 1C).

In order to rule out the possibility that Ts16 cultures contain a higher proportion of neurons that express only TrkB.T1, euploid and Ts16 cultures were analyzed by fluorescence immunocytochemistry (ICC) using anti-TrkB(T1) and anti-TrkB(in), which recognizes a unique, intracellular epitotope of the full-length TrkB isoform. All of the neurons in both euploid and Ts16 cultures expressed both TrkB.FL and TrkB.T1. The cellular distributions of the two isoforms were similar, with expression present in the plasma membrane and cytoplasm; the distributions were indistinguishable in the two genotypes. This intracellular distribution is consistent with reports that TrkB is present in both plasma membrane and intracellular locations and can be redistributed in response to physiological stimuli (Meyer-Franke A, et al., Depolarization and cAMP elevation rapidly recruit TrkB to the plasma membrane of CNS neurons, *Neuron* 21:681–693 (1998); Du J, et al., Activity- and $Ca^{2+}$-dependent modulation of surface expression of brain-derived neurotrophic factor receptors in hippocampal neurons, *J. Cell. Biol.* 150:1423–1433 (2000)).

BDNF-stimulated TrkB Phosphorylation is Reduced in Ts16 Neurons

If TrkB.T1 acts by a dominant negative mechanism to reduce TrkB signaling, there should be less BDNF-stimulated tyrosine phosphorylation of TrkB in Ts16 neurons. To test this prediction phosphorylation of TrkB was measured by western blot analysis using antibodies specific for phosphotyrosine in position Y490 in TrkB.FL. This antibody was raised to phospho-TrkA and it also recognizes the corresponding phosphorylated tyrosine in TrkB and TrkC. Because there is no detectable TrkA in mouse hippocampal neurons and any BDNF-stimulated phospho-TrkC could be distinguished on the basis of molecular size on these gels, in mouse hippocampal neurons, the BDNF-induced increase in trk phosphorylation determined with this antibody is phospho-TrkB. Euploid and Ts16 neuron cultures were preincubated without B27 for 4 hours and then in the absence or presence of 100 ng/ml BDNF for 5 minutes. Cells were subjected to western blot analysis as described above using anti-phospho-Trk (P-TrkB) or TrkB(out) (TrkB).

There was no detectable phosphorylation of TrkB in the absence of BDNF while 100 ng/ml BDNF caused a dramatic increase in TrkB phosphorylation. There was about 33% less TrkB phosphorylation in Ts16 neurons. The predicted change in BDNF/TrkB signaling via full-length homodimers for any reduction in the TrkB.FL/TrkB.T1 ratio can be computed assuming a dominant negative mechanism of inhibition by the truncated isoform (Eide et al., supra (1996)). Based on the observation that the TrkB.FL/TrkB.T1 ratio is 3.8 in euploid neurons and 1.5 in Ts16 neurons, this calculation predicts a 37% decrease in full-length TrkB homodimers and, therefore, in BDNF-stimulated TrkB autophosphorylation in the Ts16 neurons ($p<0.05$, n=4). Thus, BDNF stimulation of TrkB tyrosine phosphorylation is reduced in Ts16 neurons by an amount predicted from the measured decrease in the TrkB.FL/TrkB.T1 ratio.

Expression of Exogenous TrkB.FL in Ts16 Neurons Restores BDNF Survival Signaling Overexpression of TrkB.T1 relative to TrkB.FL could cause the failure of BDNF signaling in Ts16 neurons. In order test this hypothesis, replication-deficient adenoviruses were utilized to introduce TrkB.FL or TrkB.T1 into the neurons in order to experimentally manipulate the proportions of the two trkB isoforms. The replication-deficient adenoviruses contained DNA coding for TrkB.FL (SEQ ID NO: 9) (AdFL), TrkB.T1 (SEQ ID NO: 11) (AdTR), or no TrkB DNA (Ad-) and were generated as described above (see also Gonzalez M, supra (1999)).

Figure 3A:
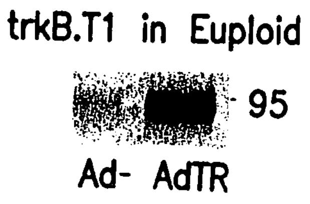
FIG. 3A is a western blot showing the level of expression of exogenous TrkB.T1 in euploid neurons exposed to adenovirus carrying TrkB.T1-HA DNA (AdTR) and euploid neurons exposed to an adenovirus control (Ad-).
Figure 3B:
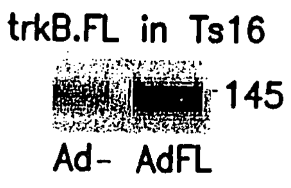
FIG. 3B shows a western blot showing the level of expression of exogenous TrkB.FL in Ts16 neurons exposed to adenovirus carrying TrkB.FL-HA DNA (AdFL) and Ts16 neurons exposed to an adenovirus control (Ad-).

Euploid and Ts16 neurons infected with AdTR expressed increased levels of TrkB.T1 as detected by either anti-TrkB (out) or anti-TrkB(T1) (TrkB.T1 in euploid neurons illustrated in FIG. 3A). In FIG. 3A, euploid neurons were exposed to adenovirus carrying TrkB.T1-HA DNA (AdTR) resulting in expression of TrkB.T1 detected on western blots, at 95 kDa, using anti-TrkB(out). Anti-HA ICC revealed that the exogenous TrkB.T1 was expressed in the plasma membrane and cytoplasm. Similarly, euploid and Ts16 neurons infected with AdFL expressed increased amounts of TrkB.FL (TrkB.FL in Ts16 neurons illustrated in FIG. 3B). In FIG. 3B, Ts16 neurons were exposed to adenovirus carrying TrkB.FL-HA DNA (AdFL) resulting in expression of TrkB.FL detected on western blots using anti-TrkB(out). Anti-HA ICC revealed that like exogenous TrkB.T1, exogenous TrkB.FL was expressed in the plasma membrane and cytoplasm. ICC using anti-HA revealed that 75% of the neurons expressed exogenous TrkB.T1 or TrkB.FL, moreover, examination of expression of the HA tag by fluorescence confocal ICC revealed that most of the exogenous TrkB.T1 and TrkB.FL in infected neurons was located on the plasma membrane. Ad– did not affect levels or distribution of endogenous TrkB. FL and TrkB.T1.

Figure 3C:
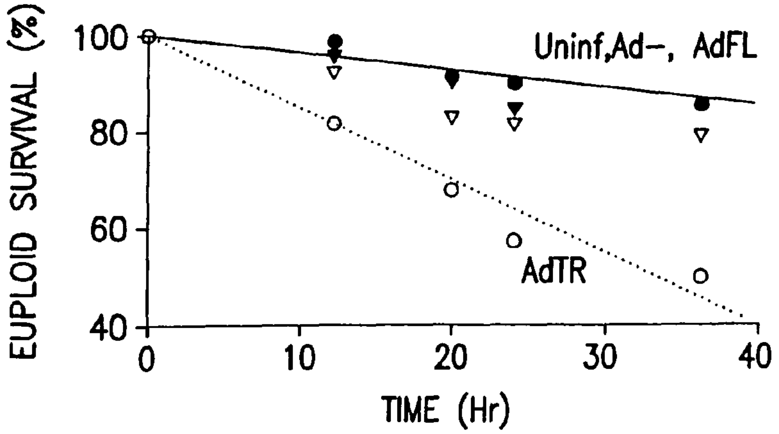
FIG. 3C illustrates the survival of neurons infected with adenovirus control (Ad-) (▼), adenovirus carrying TrkB.FL- HA DNA (AdFL) (∇), and adenovirus carrying TrkB.T1-HA DNA (AdTR) (○), and untreated neurons (●). The expression of TrkB.T1 in euploid neurons inhibits BDNF survival signaling.

Neuron survival was studied in cultures infected with Ad-, AdFL and AdTR (FIGS. 3C, D, E). Time courses of neuron survival in the presence of BDNF are shown for euploid (FIG. 3C) and Ts16 (FIG. 3D) neurons. Ad- and AdFL did not substantially affect the BDNF-induced survival of euploid neurons. In contrast, AdTR, which raised TrkB.T1 expression (FIG. 3A), increased the rate of euploid neuron death (FIG. 3C, dotted line) to a level approximately equal to the rate of death of uninfected Ts16 neurons in the presence of BDNF (100 ng/ml). In FIG. 3C, expression of TrkB.T1 in euploid neurons inhibited BDNF survival signaling. Euploid neurons were either left untreated (•, Uninf) or treated with Ad− (t), AdFL (Ñ) or AdTR (O) at 2 days in vitro. At 3 days in vitro, B27 was withdrawn from the cultures and 100 ng/ml BDNF was added. Surviving neurons were repeatedly counted in 5 identified fields on each of two coverslips per condition. 250–400 neurons were counted for each data point. In FIG. 3C, the solid line represents a linear regression for data for the untreated neurons, and the dotted line represents a linear regression for AdTR-treated neurons.

Figure 3D:
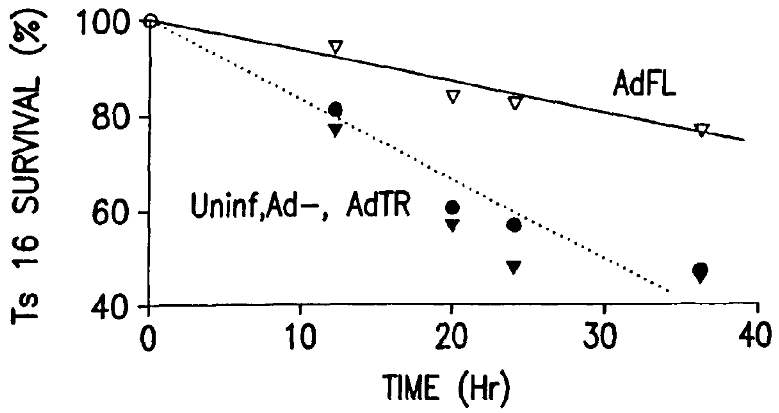
FIG. 3D illustrates the survival of Ts16 neurons infected with adenovirus control (Ad−) (▼), adenovirus carrying TrkB.FL-HA DNA (AdFL) (∇), and adenovirus carrying TrkB.T1-HA DNA (AdTR) (○), and untreated neurons (●). The expression of TrkB.FL in Ts16 neurons neurons restores BDNF survival signaling.

When added to Ts16 cultures (FIG. 3D), AdTR slightly increased the rate of neuron death while Ad− had no effect. In contrast, AdFL increased Ts16 neuron survival in the presence of BDNF to the level of survival of euploid neurons in the presence of BDNF (FIG. 3D, dotted line). In FIG. 3D, the expression of TrkB.FL in Ts16 neurons restored BDNF survival signaling. Ts16 neurons were either untreated (•, Uninf) or treated with Ad− (t) AdTR (O) or AdFL (Ñ) at 2 days in vitro. At 3 days in vitro, B27 was withdrawn from the cultures and 100 ng/ml BDNF was added. Surviving neurons were repeatedly counted in 5 identified fields on each of two coverslips under each condition. 250–400 neurons were counted for each data point. In FIG. 3D, the solid line represents a linear regression for data for the untreated neurons, and the dotted line represents a linear regression for AdFL-treated neurons.

Figure 3E:
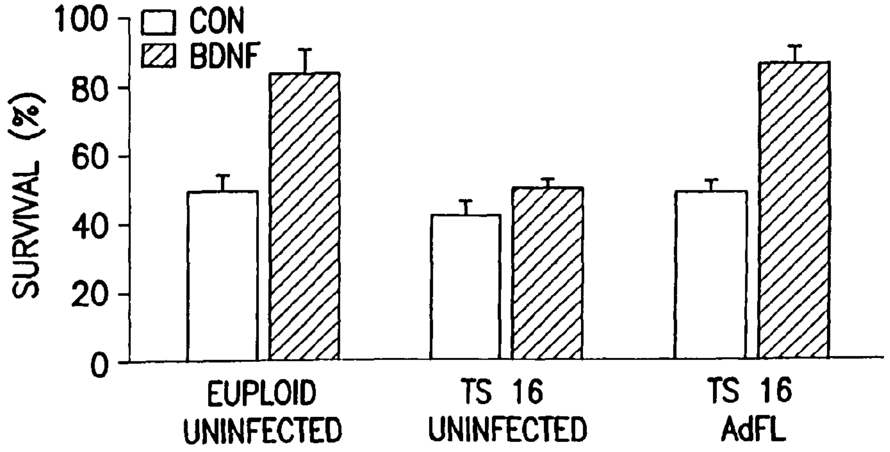
FIG. 3E summarizes the effect of TrkB.FL expression on BDNF survival signaling; the survival of euploid neurons (with and with BDNF treatment), Ts16 neurons (with and without BDNF treatment), and Ts16 neurons (with and without BDNF treatment) is shown.

The essential findings of the effect of TrkB.FL expression on BDNF survival signaling are summarized in FIG. 3E. Data show mean±sem (n=3 experiments) survival 36 hours after B27 withdrawal. About half of the untreated euploid neurons died in the absence of 100 ng/ml BDNF while fewer than 20% died in its presence. BDNF did not increase survival of untreated Ts16 neurons, however, in Ts16 neurons treated with AdFL, BDNF elicited a survival response that was indistinguishable from that of euploid neurons. BDNF reverses approximately 65% of the euploid neuron death induced by B27 withdrawal but has no effect on Ts16 neuron survival. Infection of Ts16 neurons with AdFL, which raises expression of TrkB.FL (FIG. 3B), completely restores the ability of BDNF to rescue the Ts16 neurons. In addition, raising TrkB.FL in Ts16 neurons also prevents the appearance of fragmented neurites, a characteristic of early stages of neuronal apoptosis. Cultured neurons were incubated in the absence of B27 and the presence of 100 ng/ml BDNF for 36 hours and then immunostained for MAP2ab using a rhodamine-conjugated secondary antibody. Most euploid neurons had smooth neurites. In contrast, many surviving Ts16 neurons had fragmented neurites indicative of early neurodegeneration. Ts16 neurons treated with AdFL had very few fragmented neurites and the cultures were morphologically indistinguishable from euploid neurons.

These results demonstrate that a chromosomal abnormality in mice (Ts16) with considerable similarity to DS (Ts21) results in the selective failure of BDNF-induced survival signaling. Not wishing to be bound by theory, this failure appears to be result from the elevated expression of a truncated isoform of the BDNF receptor, TrkB. Without excluding a role for signaling by TrkB.T1 (Haapasalo A, et al., Expression of the naturally occurring truncated trkB neurotrophin receptor induces outgrowth of filopodia and processes in neuroblastoma cells, *Oncogene* 18: 1285–1296 (1999), Baxter G T, et al., Signal transduction mediated by the truncated trkB receptor isoforms, trkB.T1 and trkB.T2, *J. Neurosci.* 17:2683–2690 (1997)), it is clear that elevated expression of TrkB.T1 in Ts16 neurons would reduce BDNF signaling by forming TrkB.T1-TrkB.FL heterodimers that are incapable of signaling to downstream effectors due to the absence of trans-tyrosine auto-phosphorylation (Eide F F, et al., supra (1996); Gonzalez M, et al., supra (1999); Ichinose and Snider, Differential effects of TrkC isoforms on sensory axon outgrowth, *J. Neurosci. Res.* 59:365–371 (2000); Yacoubian and Lo, Truncated and full-length TrkB receptors regulate distinct modes of dendritic growth, *Nature Neurosci. Res.* 3:342–349 (2000)). It is of interest that the TrkB.FL/TrkB.T1 ratio in Ts16 neurons (FIG. 2B) predicts only a 37% decrease in trk phosphorylation (Eide F F, et al., supra (1996)). This predicated decrease is consistent with the finding of BDNF-induced TrkB phosphorylation in both euploid and Ts16 neurons, indicating that some of the TrkB.FL in Ts16 neurons does form functionally active homodimers (western blotting with anti-phospho-trk).

It is of interest that TrkB.T1 is elevated in hippocampal and cortical neurons of AD patients (Ferrer I, et al., BDNF and full-length and truncated TrkB expression in Alzheimer disease. Implications in therapeutic strategies, *J. Neuropathol. Exp. Neurol.* 58:729–739 (1999)). By altering the expression of truncated trkB and full length trkB in AD patients, one may be able to treat AD patients.

BDNF regulates other neural functions including the generation and differentiation of neurons during development, axon growth and growth cone mobility, and synaptic plasticity (Lu supra (1999)). If one or more of these BDNF-mediated responses were affected in DS because of elevated truncated trkB expression, cognitive function could be compromised due to errors in connectivity and the failure to properly modulate synaptic plasticity, even before significant numbers of neurons are lost. Such deficits could contribute to mental retardation and premature AD in this disorder. However, increasing the level of expression of full-length trkB or reducing the amount of truncated TrkB polypeptides in the neurons may prevent some or all of the cognitive function impairment. Improved connectivity and modulation of synaptic plasticity may result from increasing the amount of full-length TrkB expressed in neurons or decreasing the amount of truncated TrkB expressed in neurons.

The importance of neurotrophins in maintaining neuron survival has led to attempts to introduce neurotrophins into the brain in order to treat neuro-degenerative disorders such as AD and Parkinson's disease (Lu, supra (1999)). The results reported here raise the possibility that failure of neurotrophin signaling may contribute to some neuro-degenerative disorders and, consequently, affected neurons may not respond to therapies designed to raise neurotrophin levels in the brain. Finally, the ability to reverse a naturally-occurring failure to respond to a neuron survival factor by introducing a particular isoform of its receptor suggests potential therapeutic strategies for treatment of neuro-degenerative disorders.

Reduction of TrkB.T1 Levels in Ts16 Neurons

In order to reduce the amount of TrkB.T1 polypeptide in Ts16 neurons, one can express within the neuron or administer to the neuron anti-sense RNA whereby the anti-sense RNA is complementary to a portion of the TrkB.T1 nucleotide sequence that is specific to the truncated isoform. Also, one can express within a neuron or administer to a neuron double-stranded RNA with sequences specific for TrkB.T1.

These methods will result in a measurable decrease (by western blot) in the amount of TrkB.T1 isoform present in the neurons.

A. Adenovirus Mediated Administration

To express anti-sense RNA in Ts16, any of the above mentioned viral vectors can be used to introduce the polynucleotide into the cells. In one example, one can use adenovirus containing 1089 base pair of DNA (SEQ ID NO: 17) which one uses to generate anti-sense RNA. The 1089 base pair anti-sense RNA is complementary to the mRNA for TrkB.T1 in the unique T1 intracellular domain and 3' UTR regions. The anti-sense RNA for this example is the same as SEQ ID NO: 17 but with uracil instead of thymine. It is possible to use shorter lengths of DNA in the adenovirus to generate shorter anti-sense RNA, so long as the adenovirus generates an anti-sense RNA that is complementary to the mRNA in a region specific for T1. An adenovirus vector containing the anti-sense RNA sequences is generated generally as described above (see also Gonzalez et al., supra (1999)) except that the DNA sequences encodes the anti-sense RNA (SEQ ID NO: 17) for mouse TrkB.T1. No HA and GFP sequences need to be added to the adenovirus. This construct is designated AdTR.anti. Adenovirus mediated transgene expression and function are evaluated by western blot and in a PC12 neurite outgrowth assay as described supra.

Ts16 neurons infected with AdTR.anti have reduced levels of truncated TrkB as determined by western blot (as described above) using either anti-TrkB(out) or anti-TrkB (T1).

Neuron survival is studied in cultures of Ts16 neurons infected with ADTR.anti. Time courses of neuron survival in the presence of BDNF indicate that Ts16 neurons infected with AdTr.anti have better survival compared to Ad− nfected Ts16 neurons. For survival studies, Ts16 neurons are infected with AdTr.anti or Ad− at 2 days in vitro. At 3 days in vitro, B27 is withdrawn from the cultures and 100 ng/ml of BDNF is added. Surviving neurons are repeated counted in 5 identical fields on each of two coverslips per condition. 250–400 neurons are counted for each data point. Thus, the reduction in the amount of TrkB.T1 in Ts16 neurons leads to improved survival of the cells.

B. Addition of Anti-Sense RNA Oligos to Media Administration

Administration of anti-sense RNA can occur via the addition of oligos of RNA (ranging in length from 10 mer to 45 mer, and more preferably from 18 mer to 25 mer) to the cell culture media at a concentration of 0.1 mM to 500 mM, more preferably between 1 mM to 50 mM. The cells in culture are Ts16 neurons, isolated as described above. The anti-sense oligonucleotide administered is specific to the T1 isoform of truncated Trk.B. One possible sequence is AAGCAGGCUG CAGACAUCCU (SEQ ID NO: 18). It is possible to use thymine instead of uracil in the anti-sense RNA. This sequence can be produced using any known in the art nucleotide generators (Oligos Etc., Wilsonville, Oreg.).

One to five days after addition of the anti-sense RNA oligos to the cell culture media which contains B27, the Ts16 cells are harvested and the amount of TrkB.T1 isoform present in the cells is determined via western blot (as described above) using either anti-TrkB(out) or anti-TrkB (T1). The amount of TrkB.T1 isoform in the Ts16 neurons with anti-sense RNA oligos added to the cell culture media decreases compared to untreated Ts16 neurons with no effect on the amount of full-length TrkB.

To test increased survival of Ts16 neurons having anti-sense RNA added to the cell culture media, the Ts16 neurons are kept in culture with between 1 mM to 50 mM anti-sense RNA (SEQ ID NO: 18) for five days. After five days of culture in B27 supplemented media with anti-sense RNA, the B27 and anti-sense RNA are removed and 100 ng/ml of BDNF is added along with anti-sense RNA (1 mM to 50 mM). Surviving neurons are counted daily in 5 identical fields on each of two coverslips per condition. 250–400 neurons are counted for each data point. The addition of anti-sense RNA oligos to the cell culture media increases the survival of the Ts16 neurons compared to the survival of untreated Ts16 neurons.

C. RNA Interference (RNAi) via Adenovirus Administration

Eukaryotic gene expression can be effectively inhibited by double-stranded RNA molecules. It is generally accepted in the art-field that the double-stranded RNA molecules efficiently inactivate transcribed genes for long periods of time. This process is called RNA interference (RNAi) or RNA silencing. Double-stranded RNA can be introduced into neurons via adenovirus mediated gene therapy, electroporation, micro-injection, or calcium phosphate precipitation, or any of the other methods described above.

Use of replication-defective adenovirus may be particularly useful in this method. Any of the sequences described for anti-sense RNA adenovirus gene therapy or anti-sense RNA oligos can be cloned into replication-defective adenovirus vectors as described above. In addition, another promoter (such as neuron-specific enolase) is cloned into the 3' end of the DNA sequence such that the promoter is orientated to drive transcription of the negative or complementary DNA strand, thereby allowing generation of two complementary strands of MRNA which can then hybridize and form double-stranded RNA.

Treatment or Prevention of Neuro-degenerative Disorders and Neuro-developmental Disorders The above experiments indicate that one can increase the survival of Ts16 neurons by either increasing the amount of full-length TrkB or decreasing the amount of truncated TrkB in the neurons. Because Ts16 is a well-known mouse model for Downs Syndrome and because neurons for various human neurogenerative diseases lack an ability to survive even when BDNF, NT-4/5, and NT-3 are administered, it is proposed that altering the level of truncated isoforms of TrkB and/or TrkC in cells may treat or prevent various neuro-degenerative diseases. One can decrease the levels of truncated TrkB and/or TrkC in cells by using anti-sense RNA and/or double-stranded RNA technology and gene therapy. Alternatively, one can increase the levels of full-length TrkB and/or TrkC in cells by using gene therapy. Alternatively, one can both decrease the level of expression of truncated TrkB and/or TrkC while, at the same time, increasing the level of expression of full-length TrkB and/or TrkC.

It is possible to treat neuro-degenerative disorders and neuro-developmental disorders by altering the ratio of the amount of human full-length TrkB (TrkB.FL) polypeptide (SEQ ID NO: 2) to human truncated TrkB isoform TrkB.T1 polypeptide (SEQ ID NO: 4) and/or human truncated TrkB isoform TrkB.Shc (SEQ ID NO: 6) in cells. One can increase this ratio by increasing the amount of full-length TrkB polypeptide and/or decreasing the amount of truncated TrkB polypeptides (either TrkB.T1 or TrkB.Shc or a combination of both). One can decrease this ratio by increasing the amount of truncated TrkB polypeptides (either TrkB.T1 or TrkB.Shc or a combination of both) and/or decreasing the amount of full-length TrkB polypeptide.

One can increase the amount of full-length TrkB protein in neurons by getting DNA into neurons by using any of the methods of administration described above. For example, DNA encoding for human full-length TrkB (SEQ ID NO: 2) can be cloned into a replication-defective adenovirus as described above. Then $10^3$ to $10^8$ plaque forming units of the adenovirus vector can be administered intra-nasally on a monthly basis.

In the event that one desires to selectively induce apoptosis, then one can take a similar approach as described above but instead increase the amount of truncated TrkB protein (TrkB.T1 and/or TrkB.Shc) expressed in cells. DNA encoding for TrkB.T1 (SEQ ID NO: 4) or TrkB.Shc (SEQ ID NO: 6) is cloned into a replication-defective adenovirus as described above. Then $10^3$ to $10^8$ plaque forming units of the adenovirus vector can be administered intra-nasally on a monthly basis.

It is possible to decrease the amount of truncated TrkB protein in a cell by using any of the above mentioned vectors or techniques. One would need to utilize the human TrkB.T1 and/or human TrkB.Shc sequences which are described above.

Similarly, if one desires to selectively induce apoptosis, then one can take a similar approach as described above using double-stranded RNA or anti-sense RNA specific for full-length TrkB or TrkC to decrease the amount of full-length TrkB protein or full-length TrkC protein in cells.

In addition to altering the ratio of the amount of full-length TrkB protein to the amount of truncated TrkB proteins in cells or the ratio of the amount of full-length TrkC protein to the amount of truncated TrkC proteins in cells, one may also administer growth factors (such as BDNF, NT-3, NT-4/5, B27, or other neurotrophins) or antagonists or agonists which bind to the TrkB receptor or TrkC receptor to help in the treatment and/or prevention of the neuro-degenerative or neuro-developmental disorders or other diseases.

It is also understood that TrkB and TrkC are expressed in various tissues in addition to neuronal tissue. Diseases which adversely affect these tissues can be treated in a similar manner as described above by altering the ratio of the amount of the isoform proteins present in those cells. Application of growth factors, other proteins, antagonists, and/or agonists which bind to the TrkB and/or TrkC receptors is useful to treat or prevent the diseases.

It is appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

The invention claimed is:

1. A method of increasing TrkB in a neuropathic hippocampal neuron comprising the step of: contacting a neuropathic hippocampal neuron in vitro with an amount of an isolated nucleic acid encoding full-length TrkB in an amount sufficient to increase the amount of full-length TrkB in said neuron, whereby said isolated nucleic acid is expressed in said neurons compared to a neuropathic hippocampal neuron not contacted with said isolated nucleic acid.

2. The method of claim 1, wherein said nucleic acid encodes the amino acid sequence of SEQ ID NO: 2.

3. The method of claim 1, wherein said nucleic acid comprises the nucleotide sequence of SEQ ID NO: 1.

4. A method of increasing the ratio of the amount of full-length TrkB polypeptide to truncated TrkB polypeptide in a neuropathic hippocampal neuron wherein the neuropathic hippocampal neuron has a higher amount of truncated TrkB compared to full-length TrkB polypeptide, said method comprising contacting a neuropathic hippocampal neuron in vitro with an amount of an isolated nucleic acid encoding full-length TrkB in an amount sufficient to increase the amount of full-length TrkB in said neuron.

5. The method of claim 4, wherein said vector comprises a nucleic acid encoding full-length TrkB.

6. The method of claim 4, wherein said vector is selected from the group consisting of a viral vector and a plasmid.

7. The method of claim 6, wherein said viral vector is selected from the group consisting of a herpes virus, adenovirus, adeno associated virus, retrovirus, vacccinia virus, and canary pox virus.

8. The method of claim 5, wherein said nucleic acid comprises a nucleotide sequence encoding the amino acid sequence of SEQ ID NO: 2.

* * * * *

SEQUENCE LISTING

```
<160> NUMBER OF SEQ ID NOS: 22

<210> SEQ ID NO 1
<211> LENGTH: 3707
<212> TYPE: DNA
<213> ORGANISM: Homo sapiens
<300> PUBLICATION INFORMATION:
<308> DATABASE ACCESSION NUMBER: NCBI/NM_006180
<309> DATABASE ENTRY DATE: 2000-11-01
<313> RELEVANT RESIDUES: (1)..(3707)

<400> SEQUENCE: 1

cccccattcg catctaacaa ggaatctgcg ccccagagag tcccggacgc cgccggtcgg     60

tgcccggcgc gccgggccat gcagcgacgg ccgccgcgga gctccgagca gcggtagcgc    120

ccccctgtaa agcggttcgc tatgccggga ccactgtgaa ccctgccgcc tgccggaaca    180

ctcttcgctc cggaccagct cagcctctga taagctggac tcggcacgcc cgcaacaagc    240

accgaggagt taagagagcc gcaagcgcag ggaaggcctc cccgcacggg tgggggaaag    300

cggccggtgc agcgcgggga caggcactcg ggctggcact ggctgctagg gatgtcgtcc    360

tggataaggt ggcatggacc cgccatggcg cggctctggg gcttctgctg gctggttgtg    420

ggcttctgga gggccgcttt cgcctgtccc acgtcctgca aatgcagtgc ctctcggatc    480

tggtgcagcg acccttctcc tggcatcgtg gcatttccga gattggagcc taacagtgta    540

gatcctgaga acatcaccga aattttcatc gcaaaccaga aaaggttaga aatcatcaac    600
```

-continued

```
gaagatgatg ttgaagctta tgtgggactg agaaatctga caattgtgga ttctggatta    660
aaatttgtgg ctcataaagc atttctgaaa aacagcaacc tgcagcacat caattttacc    720
cgaaacaaac tgacgagttt gtctaggaaa catttccgtc accttgactt gtctgaactg    780
atcctggtgg gcaatccatt tacatgctcc tgtgacatta tgtggatcaa gactctccaa    840
gaggctaaat ccagtccaga cactcaggat ttgtactgcc tgaatgaaag cagcaagaat    900
attcccctgg caaacctgca gatacccaat tgtggtttgc catctgcaaa tctggccgca    960
cctaacctca ctgtggagga aggaaagtct atcacattat cctgtagtgt ggcaggtgat   1020
ccggttccta atatgtattg ggatgttggt aacctggttt ccaaacatat gaatgaaaca   1080
agccacacac agggctcctt aaggataact aacatttcat ccgatgacag tgggaagcag   1140
atctcttgtg tggcggaaaa tcttgtagga gaagatcaag attctgtcaa cctcactgtg   1200
cattttgcac caactatcac atttctcgaa tctccaacct cagaccacca ctggtgcatt   1260
ccattcactg tgaaaggcaa ccccaaacca gcgcttcagt ggttctataa cggggcaata   1320
ttgaatgagt ccaaatacat ctgtactaaa atacatgtta ccaatcacac ggagtaccac   1380
ggctgcctcc agctggataa tcccactcac atgaacaatg gggactacac tctaatagcc   1440
aagaatgagt atgggaagga tgagaaacag atttctgctc acttcatggg ctggcctgga   1500
attgacgatg gtgcaaaccc aaattatcct gatgtaattt atgaagatta tggaactgca   1560
gcgaatgaca tcggggacac cacgaacaga agtaatgaaa tcccttccac agacgtcact   1620
gataaaaccg gtcgggaaca tctctcggtc tatgctgtgg tggtgattgc gtctgtggtg   1680
ggattttgcc ttttggtaat gctgtttctg cttaagttgg caagacactc caagtttggc   1740
atgaaaggcc cagcctccgt tatcagcaat gatgatgact ctgccagccc actccatcac   1800
atctccaatg ggagtaacac tccatcttct tcggaaggtg gcccagatgc tgtcattatt   1860
ggaatgacca agatccctgt cattgaaaat ccccagtact ttggcatcac caacagtcag   1920
ctcaagccag acacatttgt tcagcacatc aagcgacata acattgttct gaaaagggag   1980
ctaggcgaag gagcctttgg aaaagtgttc ctagctgaat gctataacct ctgtcctgag   2040
caggacaaga tcttggtggc agtgaagacc ctgaaggatg ccagtgacaa tgcacgcaag   2100
gacttccacc gtgaggccga gctcctgacc aacctccagc atgagcacat cgtcaagttc   2160
tatggcgtct gcgtggaggg cgacccccctc atcatggtct ttgagtacat gaagcatggg   2220
gacctcaaca agttcctcag ggcacacggc cctgatgccg tgctgatggc tgagggcaac   2280
ccgcccacgg aactgacgca gtcgcagatg ctgcatatag cccagcagat cgccgcgggc   2340
atggtctacc tggcgtccca gcacttcgtg caccgcgatt tggccaccag gaactgcctg   2400
gtcgggggaga acttgctggt gaaaatcggg gactttggga tgtcccggga cgtgtacagc   2460
actgactact acagggtcgg tggccacaca atgctgccca ttcgctggat gcctccagag   2520
agcatcatgt acaggaaatt cacgacggaa agcgacgtct ggagcctggg ggtcgtgttg   2580
tgggagattt tcacctatgg caaacagccc tggtaccagc tgtcaaacaa tgaggtgata   2640
gagtgtatca ctcagggccg agtcctgcag cgaccccgca cgtgccccca ggaggtgtat   2700
gagctgatgc tggggtgctg gcagcgagag ccccacatga ggaagaacat caagggcatc   2760
cataccctcc ttcagaactt ggccaaggca tctccggtct acctggacat tctaggctag   2820
ggcccttttc cccagaccga tccttcccaa cgtactcctc agacgggctg agaggatgaa   2880
catcttttaa ctgccgctgg aggccaccaa gctgctctcc ttcactctga cagtattaac   2940
```

-continued

```
atcaaagact ccgagaagct ctcgagggaa gcagtgtgta cttcttcatc catagacaca   3000

gtattgactt ctttttggca ttatctcttt ctctctttcc atctcccttg gttgttcctt   3060

tttctttttt taaattttct ttttcttctt ttttttcgtc ttccctgctt cacgattctt   3120

accctttctt ttgaatcaat ctggcttctg cattactatt aactctgcat agacaaaggc   3180

cttaacaaac gtaatttgtt atatcagcag acactccagt ttgcccacca caactaacaa   3240

tgccttgttg tattcctgcc tttgatgtgg atgaaaaaaa gggaaaacaa atatttcact   3300

taaactttgt cacttctgct gtacagatat cgagagtttc tatggattca cttctattta   3360

tttattatta ttactgttct tattgttttt ggatggctta agcctgtgta taaaaaagaa   3420

aacttgtgtt caatctgtga agcctttatc tatgggagat taaaaccaga gagaaagaag   3480

atttattatg aaccgcaata tgggaggaac aaagacaacc actgggatca gctggtgtca   3540

gtccctactt aggaaatact cagcaactgt tagctgggaa gaatgtattc ggcaccttcc   3600

cctgaggacc tttctgagga gtaaaaagac tactggcctc tgtgccatgg atgattcttt   3660

tcccatcacc agaaatgata gcgtgcagta gagagcaaag atggctt                 3707
```

```
<210> SEQ ID NO 2
<211> LENGTH: 822
<212> TYPE: PRT
<213> ORGANISM: Homo sapiens
<300> PUBLICATION INFORMATION:
<308> DATABASE ACCESSION NUMBER: NCBI/NM_006180
<309> DATABASE ENTRY DATE: 2000-11-01
<313> RELEVANT RESIDUES: (1)..(822)

<400> SEQUENCE: 2

Met Ser Ser Trp Ile Arg Trp His Gly Pro Ala Met Ala Arg Leu Trp
 1               5                  10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220
```

-continued

```
Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Gly Pro Ala Ser Val Ile Ser Asn Asp Asp Asp Ser Ala Ser Pro
465                 470                 475                 480

Leu His His Ile Ser Asn Gly Ser Asn Thr Pro Ser Ser Ser Glu Gly
                485                 490                 495

Gly Pro Asp Ala Val Ile Ile Gly Met Thr Lys Ile Pro Val Ile Glu
            500                 505                 510

Asn Pro Gln Tyr Phe Gly Ile Thr Asn Ser Gln Leu Lys Pro Asp Thr
        515                 520                 525

Phe Val Gln His Ile Lys Arg His Asn Ile Val Leu Lys Arg Glu Leu
    530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
        595                 600                 605

Glu Gly Asp Pro Leu Ile Met Val Phe Glu Tyr Met Lys His Gly Asp
    610                 615                 620

Leu Asn Lys Phe Leu Arg Ala His Gly Pro Asp Ala Val Leu Met Ala
625                 630                 635                 640
```

-continued

```
Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
        675                 680                 685

Leu Val Lys Ile Gly Asp Phe Gly Met Ser Arg Asp Val Tyr Ser Thr
    690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
    770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820
```

<210> SEQ ID NO 3
<211> LENGTH: 1870
<212> TYPE: DNA
<213> ORGANISM: Homo sapiens
<300> PUBLICATION INFORMATION:
<308> DATABASE ACCESSION NUMBER: NCBI/S76474
<309> DATABASE ENTRY DATE: 1995-07-25
<313> RELEVANT RESIDUES: (1)..(1870)

<400> SEQUENCE: 3

```
ggaaggttta aagaagaagc cgcaaagcgc agggaaggcc tcccggcacg ggtgggggaa     60

agcggccggt gcagcgcggg gacaggcact cgggctggca ctggctgcta gggatgtcgt    120

cctggataag gtggcatgga cccgccatgg cgcggctctg ggcttctgc tggctggttg    180

tgggcttctg gagggccgct ttcgcctgtc ccacgtcctg caaatgcagt gcctctcgga    240

tctggtgcag cgacccttct cctggcatcg tggcatttcc gagattggag cctaacagtg    300

tagatcctga gaacatcacc gaaattttca tcgcaaacca gaaaaggtta gaaatcatca    360

acgaagatga tgttgaagct tatgtgggac tgagaaatct gacaattgtg gattctggat    420

taaaatttgt ggctcataaa gcatttctga aaaacagcaa cctgcagcac atcaatttta    480

cccgaaacaa actgacgagt ttgtctagga aacatttccg tcaccttgac ttgtctgaac    540

tgatcctggt gggcaatcca tttacatgct cctgtgacat tatgtggatc aagactctcc    600

aagaggctaa atccagtcca gacactcagg atttgtactg cctgaatgaa agcagcaaga    660

atattcccct ggcaaacctg cagataccca attgtggttt gccatctgca aatctggccg    720

cacctaacct cactgtggag gaaggaaagt ctatcacatt atcctgtagt gtggcaggtg    780

atccggttcc taatatgtat tgggatgttg gtaacctggt ttccaaacat atgaatgaaa    840

caagccacac acagggctcc ttaaggataa ctaacatttc atccgatgac agtgggaagc    900

agatctcttg tgtggcggaa aatcttgtag gagaagatca agattctgtc aacctcactg    960
```

-continued

```
tgcattttgc accaactatc acatttctcg aatctccaac ctcagaccac cactggtgca   1020

ttccattcac tgtgaaaggc aacccaaaac cagcgcttca gtggttctat aacggggcaa   1080

tattgaatga gtccaaatac atctgtacta aaatacatgt taccaatcac acggagtacc   1140

acggctgcct ccagctggat aatcccactc acatgaacaa tggggactac actctaatag   1200

ccaagaatga gtatgggaag gatgagaaac agatttctgc tcacttcatg ggctggcctg   1260

gaattgacga tggtgcaaac ccaaattatc ctgatgtaat ttatgaagat tatggaactg   1320

cagcgaatga catcggggac accacgaaca gaagtaatga aatcccttcc acagacgtca   1380

ctgataaaac cggtcgggaa catctctcgg tctatgctgt ggtggtgatt gcgtctgtgg   1440

tgggattttg ccttttggta atgctgtttc tgcttaagtt ggcaagacac tccaagtttg   1500

gcatgaaagg ttttgttttg tttcataaga tcccactgga tgggtagctg aaataaagga   1560

aaagacagag aaaggggctg tggtgcttgt tggttgatgc tgccatgtaa gctggactcc   1620

tgggactgct gttggcttat cccgggaagt gctgcttatc tggggttttc tggtagatgt   1680

gggcggtgtt tggaggctgt actatatgaa gcctgcatat actgtgagct gtgattgggg   1740

aacaccaatg cagaggtaac tctcaggcag ctaagcagca cctcaagaaa acatgttaaa   1800

ttaatgcttc tcttcttaca gtagttcaaa tacaaaactg aaatgaaatc ccattggatt   1860

gtacttctct                                                          1870
```

<210> SEQ ID NO 4
<211> LENGTH: 477
<212> TYPE: PRT
<213> ORGANISM: Homo sapiens
<300> PUBLICATION INFORMATION:
<308> DATABASE ACCESSION NUMBER: NCBI/S76474
<309> DATABASE ENTRY DATE: 1995-07-25
<313> RELEVANT RESIDUES: (1)..(477)

<400> SEQUENCE: 4

```
Met Ser Ser Trp Ile Arg Trp His Gly Pro Ala Met Ala Arg Leu Trp
 1               5                  10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
```

-continued

```
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Gly Phe Val Leu Phe His Lys Ile Pro Leu Asp Gly
465                 470                 475
```

<210> SEQ ID NO 5
<211> LENGTH: 8192
<212> TYPE: DNA
<213> ORGANISM: Homo sapiens
<300> PUBLICATION INFORMATION:
<308> DATABASE ACCESSION NUMBER: NCBI/AF410900
<309> DATABASE ENTRY DATE: 2002-01-25

<400> SEQUENCE: 5

```
gggagcagga gcctcgctgg ctgcttcgct cgcgctctac gcgctcagtc cccggcggta     60

gcaggagcct ggacccaggc gccggcggcg ggcgtgaggc gccggagccc ggcctcgagg    120

tgcataccgg acccccattc gcatctaaca aggaatctgc gccccagaga gtcccggacg    180

ccgccggtcg gtgcccggcg cgccgggcca tgcagcgacg gccgccgcgg agctccgagc    240

agcggtagcg cccccctgta aagcggttcg ctatgccggg accactgtga accctgccgc    300

ctgccggaac actcttcgct ccggaccagc tcagcctctg ataagctgga ctcggcacgc    360
```

-continued

```
ccgcaacaag caccgaggag ttaagagagc cgcaagcgca gggaaggcct ccccgcacgg    420
gtgggggaaa gcggccggtg cagcgcgggg acaggcactc gggctggcac tggctgctag    480
ggatgtcgtc ctggataagg tggcatggac ccgccatggc gcggctctgg ggcttctgct    540
ggctggttgt gggcttctgg agggccgctt tcgcctgtcc cacgtcctgc aaatgcagtg    600
cctctcggat ctggtgcagc gacccttctc ctggcatcgt ggcatttccg agattggagc    660
ctaacagtgt agatcctgag aacatcaccg aaattttcat cgcaaaccag aaaaggttag    720
aaatcatcaa cgaagatgat gttgaagctt atgtgggact gagaaatctg acaattgtgg    780
attctggatt aaaatttgtg gctcataaag catttctgaa aaacagcaac ctgcagcaca    840
tcaattttac ccgaaacaaa ctgacgagtt tgtctaggaa acatttccgt caccttgact    900
tgtctgaact gatcctggtg ggcaatccat ttacatgctc ctgtgacatt atgtggatca    960
agactctcca agaggctaaa tccagtccag acactcagga tttgtactgc ctgaatgaaa   1020
gcagcaagaa tattcccctg gcaaacctgc agatacccaa ttgtggtttg ccatctgcaa   1080
atctggccgc acctaacctc actgtggagg aaggaaagtc tatcacatta tcctgtagtg   1140
tggcaggtga tccggttcct aatatgtatt gggatgttgg taacctggtt tccaaacata   1200
tgaatgaaac aagccacaca cagggctcct taaggataac taacatttca tccgatgaca   1260
gtgggaagca gatctcttgt gtggcggaaa atcttgtagg agaagatcaa gattctgtca   1320
acctcactgt gcattttgca ccaactatca catttctcga atctccaacc tcagaccacc   1380
actggtgcat tccattcact gtgaaaggca accccaaacc agcgcttcag tggttctata   1440
acggggcaat attgaatgag tccaaataca tctgtactaa aatacatgtt accaatcaca   1500
cggagtacca cggctgcctc cagctggata atcccactca catgaacaat ggggactaca   1560
ctctaatagc caagaatgag tatgggaagg atgagaaaca gatttctgct cacttcatgg   1620
gctggcctgg aattgacgat ggtgcaaacc caaattatcc tgatgtaatt tatgaagatt   1680
atggaactgc agcgaatgac atcggggaca ccacgaacag aagtaatgaa atcccttcca   1740
cagacgtcac tgataaaacc ggtcgggaac atctctcggt ctatgctgtg gtggtgattg   1800
cgtctgtggt gggattttgc cttttggtaa tgctgtttct gcttaagttg gcaagacact   1860
ccaagtttgg catgaaaggc ccagcctccg ttatcagcaa tgatgatgac tctgccagcc   1920
cactccatca catctccaat gggagtaaca ctccatcttc ttcggaaggt ggcccagatg   1980
ctgtcattat tggaatgacc aagatccctg tcattgaaaa tccccagtac tttggcatca   2040
ccaacagtca gctcaagcca gacacatggc ccagaggttc cccccaagacc gcctgataat   2100
aatttggtat ttggaggctc ctgtgtcact gcaggaacta aaggaggcta aatccatgcc   2160
tgatggagga gaagagttct atggttatct gcaaattctg gccagacaac atcttgacgt   2220
cactccttag cttccataac ctagccaagc aagaagttgc ctttccaaga caaagcagtg   2280
tgctctaatg actaacccct caaagtacta tgccacttta actatagacc catctcctcg   2340
atcaatcagg atggcaagat ggagctgagg agctcagcaa catcaagtct ggagttggtc   2400
tttaactcaa ctagctcgtt tagacgtgtc tgaacaccac atcacctgac agcacggggt   2460
ggtttcccag taaaatttac aaactcagct caagggcagc tgtgttgctt tcctttcctt   2520
gactgctgag aaactttttg acagggaaca atggaaacac accttctgag ctgaaacaaa   2580
caaacagaaa caaaacatac taaccagcaa aatccccaaa tcatcaatct tgggttctct   2640
tgaagggcag gagtgtgttt tatcttctcc cgtcggagca aacactatag atgtcctccc   2700
taaaattctg tcttccctag agcagccttg taaattagct agggtcctag ggttgaggcc   2760
```

-continued

```
taaatcaact taaaattgtc tctaaatatg tacctggatg tgtttgtact tgcagagcat   2820
gccctcttca tgtgcctagg gctagtaact ccctgtggca gaggcatgta aagtattctg   2880
actttttttt tttcaactta attccatttc caatgaaatg gatttttaaa aattttctcc   2940
agagtgtgcc atacttctcc agctattata gttaatgtgt gtgtatcctt gtgtatatgt   3000
gtgtttgtgt gtgcatatgt gttttcctag tggttacatg cttactaggc aattatgtaa   3060
ataagcacag attcataggc cagctaggcc tgaggaaaga agacattata aagggaggga   3120
gtattttaac attagctaaa gctatcacac aaggcaccca ttctgctccc ctcaacagcc   3180
acagcccact tcgtccttgt cttaccaata aggggaaagg ctggaggtga tatttttcac   3240
agaaccgcag aggttttgaa catatttgca acattacttt gagtacacat gagcaaaaat   3300
tctgaattac atccaggacc ccagaagctc attagatcaa agagtgcggg gcccctcaga   3360
gttaccagag attatctgca gacttcagtg caatcgaatg accatggtcc attttgatgg   3420
tcagaggtag gactgaaaaa cgggtagaaa caattgcttt agcgcttcct tctgtacttt   3480
gcctattaat gttttgtctt tcaaaaatat attttctcct aattgtttaa ttggccaaat   3540
aatggctgct ttgggagttg tttgtatgcc ttggaaggcc atggcctgca ctttaaaaat   3600
aagctaagtc cattctgccc agcacgagca ttaggacaga gaatgcactt attttaggat   3660
ccttaaaaat tgcttctttt atggcacact gggttgacga ctcatctcgt gggagccttc   3720
atggcacatt gctgctgttc tgcaggtccc aatacaattc cttccccctc tcagtgccac   3780
ggccccccca ttgctagcta cacaatttga tatcatattc ccttttcaac tccaaaggag   3840
atgataagaa gctatcaaat aatgctttaa aaaagcaact tgagtttctt aaaagaaagg   3900
aaatgaatac atgctgcata attacattta aaatgtaagc catgttatta taagccgcac   3960
tgagatgaag atttgttagc aaaccagttt caagcacact cacagtgaag taaaatcatg   4020
tttttagcat ctgaccattg ggtaatatta ttctttgtta tcaaaagaga aatatcaccc   4080
aagtatagta tacttagacc tcctagagga aacactccag tcctaagctt ggtgtctgaa   4140
aagaaaaaca aaaataaaga ttatggattt aggtcaggga gacagagtga tattctgaag   4200
actgtgttta ctccctcatc atcggccaac caagatggag ttctgcatcc tgcacatatc   4260
agacatttca gtccaatttc accaaagcat cagtgatgtt ctagaagcat cccagcagat   4320
ggaggatcct aatgtatttg ttctgggtat ttcccaaggc ccagcctgac tggagtgtgt   4380
gtaccaacag gatgaatcca atcaagctac gcccccattt tggtttcgga ttggccactc   4440
ttgcatgtgc tagtagattg tggaccagga ccagctgagc aaacacagtt gcagagtagc   4500
ctcctatgtt gctaagaagc tcctgctacc caggtgcttt gaacaattga gtgctccctc   4560
tggttaagta gagatggcac caccggagtt tttcttggat gtgaggctca atcctttacg   4620
gcagctatta taacaaagtg aaggttttct ccctgggaaa tgcagctttt ctctgtcttt   4680
actaattctg ccagcctgtg agagtaacca ccgtagctgg gcttcttctc agattaattg   4740
tcatgccagg tctccttcct ggggagctgt gatgctgctc tgaggttgat tgctgaggtt   4800
gtagtgggtt tttgtttgtt tttgtttagt ttttcttgat tgttcttctt tctcttgaat   4860
ggcaagagaa gaaacacttt ctctaaccca cggccaggaa ggaaatgggg agagagctac   4920
ttcttagttc aacctggttg ccacataaag gaatctctct ccttggactc agcccctaac   4980
tggaagcaag agccactgcc ctctgagact gagagagcag cccgaggagg agatgaatcc   5040
attctgccct ttgtttgggt ttgcttcctg tcagtgagag aatgctgagg cagttcctgt   5100
```

-continued

```
tatgtgaaac tttcattttt aaaaccagga cagtcctaaa cagactggaa tgagttggtc   5160
aatcccagtt ggtataggcc caatgatttt tgctagtaag ataggattgt cttcctcacc   5220
caaaatgcct tcaagtgccc taaaatgggt attttaaaat aagaataaat aatgtagatt   5280
tagtagaaaa cctggaaaac ataagaaaca aagatgaaac gaaaagtccc atgtaattcc   5340
accagttaga gttaaccact gatatcgttt ggatatatgg ctttctagtc ttgtggatat   5400
ccttttaatc tcttgtaata taaagtctga ccatatgtgt ccttgcattt gtttgtactg   5460
gactctgtta atatttctat agtaatggct cactttgggg agattgtgct gcacagtgtg   5520
taggaagcac attgggtgta ttattcccag ttttgtattt tgtatttcct tggagatgtg   5580
caggggttaa gagcgggggt ctggccatag ctggccacgt cagactctca tatggtaagt   5640
atcacagagc acatgaggcc tgtgttatgc gctggaaaga ctcaggaaat gagaggctct   5700
cttgttctga caaggcaggc tgagagctct catttagggt catcactcca gataactcca   5760
aatgcagttt attgctcaac tgaagcagat gatcactttt tgcctccaag ttcttcaccc   5820
tagctagctc ctttcaaaga gccgagtatg ctggatctta aagggccaaa ctagttacat   5880
ctcatacatt tcctgatgtt tagggatgcc ttcacttcca tcaaggatac cttggctgtg   5940
caaggacctc tgatagctgg agtctccttt tggtcactcc cagctttgct taaacttgat   6000
ggagtttgct gtccagtgat ccccggatct ttcatcatga aagccttcct tcctctcctg   6060
atgtctcagg cctctagacc tagactgggg ttctggcaag gaggcctcta tcaatagtat   6120
gacatccaat aatatgttag tgttgatatt ttgcacagta atattaagtt taagagatta   6180
taaaaatgag ttcaaatgaa taagttcctg tgatgtaaga gattagatat gtgtgatttc   6240
agaaccaaag ccagggggga atcccagaaa gaaaacaata atataatcct agtttctata   6300
tattattttt attcattact gtatatgggt agagatcaat attctttctt atgctgttac   6360
tattaattaa cacatttttt aaccatgcca ttgaactttt gggtgcatta aagtggaacc   6420
caagctcctc attagataat aatggcattt ggactgagtg ccatattcct aaatttccaa   6480
taaagtggtt gatatagaga ggacaggata aagccctata gtgtgcagtt atatcaaaac   6540
agctagtctc cactttaggg aatgccttta ctagagatta catgaaatgt ctgcttataa   6600
aataagcaga gatggtacca ctaagcagcc acctgaattg ttttcctaca ggaatgatta   6660
cttttcagat ccatttatgt tttcatgctc aatacttact ccccttccct gcaacaccca   6720
aagagtttac ttttgcaagt catttggtct tcagtctact actgaggaat agagaggcac   6780
taactgcttt acccaggatc agaactcatg ttcttacctt ctattaatag agtacttgag   6840
ccagatggac taactggtct cacattttct ctatcttggt tttacttcca taaacatcaa   6900
tatctttacc cacatgattt ttccatcctc ccattttttt ccatatgtat tagggttcag   6960
gaactatgat gctaatgatc acatttcttc ctagttccta atttcattag tgccatttcc   7020
tgatatctac agaaacaatt atcaatacat gtagctgctt gagccttatt tagaaggcta   7080
gcctttcttt tccaagtgct gtcagaatgt atacatttag tctgtctttt tccctttag    7140
gagtctttgt tctgggttga tggcaaaatt cctcttttta catgtgagat ttttgatttc   7200
actgaattct acctagattt ttatggacat tggattttaa agaggaaaac actcattttc   7260
ttagtaagat attggtgata catagctatg ccattgattt ccatactcct gagctttggg   7320
gagggagaca gtggccaagt agcaggcaga ataagatcat cactcatgtc ctgaatcaat   7380
cacactttcc ttctcggatt gtgtatatgc tctgccactt cctacatatt acatcctgag   7440
tttttaagta aagtggatct tagccagatt tgagtctaat ggctgattca tcggcatagt   7500
```

-continued

```
tcttggcgtt aacatctcag tgtcctcttt agttctcttt gaggattcat gtcattgagg   7560

gcctttgtgc ctccacttgt ctcagtatga ggaagaactt tggtgtgagg gcggagctat   7620

gtgaagggtt gctgggttgg gggattagtt catatggtcc ccatgccatc tatttacttt   7680

tggagagagg ggactttgag tgggtgggta tggatagatg ttcctcaagg aaaccctgct   7740

ggctaatggg cactacatct gtgtattact gtgattctct ctgtaagctc cccatgtggc   7800

caaggacccc cctcctacca gggcacttcc tgccacctca ttgcactggt ctcaaccatt   7860

cagcctgctg ctgctgcacc atgttgggct gcggtaggat agggaagggg ttctgttgat   7920

tgctaaatgt tgcctaactt tatttccctc tcccacattt catgcaaggg agcggaccta   7980

acacatgact tgcattctct tcctatgttc agaaactcca gggcttgccc acgtgtatgt   8040

atgagtgacc aatggagctt ggaattcttt atctatatga tctgtccgaa aatgagatct   8100

tttgtactgg aatttgtgat gtagttgatc attcagagcc aaacgcatat accaataaag   8160

acaagactgt catataaaaa aaaaaaaaaa aa                                 8192
```

```
<210> SEQ ID NO 6
<211> LENGTH: 537
<212> TYPE: PRT
<213> ORGANISM: Homo sapiens
<300> PUBLICATION INFORMATION:
<308> DATABASE ACCESSION NUMBER: NCBI/AF410900
<309> DATABASE ENTRY DATE: 2002-01-25

<400> SEQUENCE: 6

Met Ser Ser Trp Ile Arg Trp His Gly Pro Ala Met Ala Arg Leu Trp
 1               5                  10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
```

-continued 225 230 235 240

Asn Glu Thr Ser His Thr Gln Gly Ser Leu Arg Ile Thr Asn Ile Ser
245 250 255

Ser Asp Asp Ser Gly Lys Gln Ile Ser Cys Val Ala Glu Asn Leu Val
260 265 270

Gly Glu Asp Gln Asp Ser Val Asn Leu Thr Val His Phe Ala Pro Thr
275 280 285

Ile Thr Phe Leu Glu Ser Pro Thr Ser Asp His His Trp Cys Ile Pro
290 295 300

Phe Thr Val Lys Gly Asn Pro Lys Pro Ala Leu Gln Trp Phe Tyr Asn
305 310 315 320

Gly Ala Ile Leu Asn Glu Ser Lys Tyr Ile Cys Thr Lys Ile His Val
325 330 335

Thr Asn His Thr Glu Tyr His Gly Cys Leu Gln Leu Asp Asn Pro Thr
340 345 350

His Met Asn Asn Gly Asp Tyr Thr Leu Ile Ala Lys Asn Glu Tyr Gly
355 360 365

Lys Asp Glu Lys Gln Ile Ser Ala His Phe Met Gly Trp Pro Gly Ile
370 375 380

Asp Asp Gly Ala Asn Pro Asn Tyr Pro Asp Val Ile Tyr Glu Asp Tyr
385 390 395 400

Gly Thr Ala Ala Asn Asp Ile Gly Asp Thr Thr Asn Arg Ser Asn Glu
405 410 415

Ile Pro Ser Thr Asp Val Thr Asp Lys Thr Gly Arg Glu His Leu Ser
420 425 430

Val Tyr Ala Val Val Val Ile Ala Ser Val Val Gly Phe Cys Leu Leu
435 440 445

Val Met Leu Phe Leu Leu Lys Leu Ala Arg His Ser Lys Phe Gly Met
450 455 460

Lys Gly Pro Ala Ser Val Ile Ser Asn Asp Asp Asp Ser Ala Ser Pro
465 470 475 480

Leu His His Ile Ser Asn Gly Ser Asn Thr Pro Ser Ser Ser Glu Gly
485 490 495

Gly Pro Asp Ala Val Ile Ile Gly Met Thr Lys Ile Pro Val Ile Glu
500 505 510

Asn Pro Gln Tyr Phe Gly Ile Thr Asn Ser Gln Leu Lys Pro Asp Thr
515 520 525

Trp Pro Arg Gly Ser Pro Lys Thr Ala
530 535

<210> SEQ ID NO 7
<211> LENGTH: 8240
<212> TYPE: DNA
<213> ORGANISM: Homo sapiens
<300> PUBLICATION INFORMATION:
<308> DATABASE ACCESSION NUMBER: NCBI/AF410901
<309> DATABASE ENTRY DATE: 2002-01-25

<400> SEQUENCE: 7
gggagcagga gcctcgctgg ctgcttcgct cgcgctctac gcgctcagtc cccggcggta 60
gcaggagcct ggacccaggc gccggcggcg ggcgtgaggc gccggagccc ggcctcgagg 120
tgcataccgg acccccattc gcatctaaca aggaatctgc gccccagaga gtcccggacg 180
ccgccggtcg gtgcccggcg cgccgggcca tgcagcgacg gccgccgcgg agctccgagc 240
agcggtagcg ccccccctgta aagcggttcg ctatgccggg accactgtga accctgccgc 300

-continued

```
ctgccggaac actcttcgct ccggaccagc tcagcctctg ataagctgga ctcggcacgc    360
ccgcaacaag caccgaggag ttaagagagc cgcaagcgca gggaaggcct ccccgcacgg    420
gtgggggaaa gcggccggtg cagcgcgggg acaggcactc gggctggcac tggctgctag    480
ggatgtcgtc ctggataagg tggcatggac ccgccatggc gcggctctgg ggcttctgct    540
ggctggttgt gggcttctgg agggccgctt tcgcctgtcc cacgtcctgc aaatgcagtg    600
cctctcggat ctggtgcagc gacccttctc ctggcatcgt ggcatttccg agattggagc    660
ctaacagtgt agatcctgag aacatcaccg aaattttcat cgcaaaccag aaaaggttag    720
aaatcatcaa cgaagatgat gttgaagctt atgtgggact gagaaatctg acaattgtgg    780
attctggatt aaaatttgtg gctcataaag catttctgaa aaacagcaac ctgcagcaca    840
tcaattttac ccgaaacaaa ctgacgagtt tgtctaggaa acatttccgt caccttgact    900
tgtctgaact gatcctggtg ggcaatccat ttacatgctc ctgtgacatt atgtggatca    960
agactctcca agaggctaaa tccagtccag acactcagga tttgtactgc ctgaatgaaa   1020
gcagcaagaa tattcccctg gcaaacctgc agatacccaa ttgtggtttg ccatctgcaa   1080
atctggccgc acctaacctc actgtggagg aaggaaagtc tatcacatta tcctgtagtg   1140
tggcaggtga tccggttcct aatatgtatt gggatgttgg taacctggtt tccaaacata   1200
tgaatgaaac aagccacaca cagggctcct taaggataac taacatttca tccgatgaca   1260
gtgggaagca gatctcttgt gtggcggaaa atcttgtagg agaagatcaa gattctgtca   1320
acctcactgt gcattttgca ccaactatca catttctcga atctccaacc tcagaccacc   1380
actggtgcat tccattcact gtgaaaggca accccaaacc agcgcttcag tggttctata   1440
acggggcaat attgaatgag tccaaataca tctgtactaa aatacatgtt accaatcaca   1500
cggagtacca cggctgcctc cagctggata atcccactca catgaacaat ggggactaca   1560
ctctaatagc caagaatgag tatgggaagg atgagaaaca gatttctgct cacttcatgg   1620
gctggcctgg aattgacgat ggtgcaaacc caaattatcc tgatgtaatt tatgaagatt   1680
atggaactgc agcgaatgac atcggggaca ccacgaacag aagtaatgaa atcccttcca   1740
cagacgtcac tgataaaacc ggtcgggaac atctctcggt ctatgctgtg gtggtgattg   1800
cgtctgtggt gggattttgc cttttggtaa tgctgtttct gcttaagttg gcaagacact   1860
ccaagtttgg catgaaagat ttctcatggt ttggatttgg gaaagtaaaa tcaagacaag   1920
gtgttggccc agcctccgtt atcagcaatg atgatgactc tgccagccca ctccatcaca   1980
tctccaatgg gagtaacact ccatcttctt cggaaggtgg cccagatgct gtcattattg   2040
gaatgaccaa gatccctgtc attgaaaatc cccagtactt tggcatcacc aacagtcagc   2100
tcaagccaga cacatggccc agaggttccc ccaagaccgc ctgataataa tttggtattt   2160
ggaggctcct gtgtcactgc aggaactaaa ggaggctaaa tccatgcctg atggaggaga   2220
agagttctat ggttatctgc aaattctggc cagacaacat cttgacgtca ctccttagct   2280
tccataacct agccaagcaa gaagttgcct ttccaagaca aagcagtgtg ctctaatgac   2340
taacccctca aagtactatg ccactttaac tatagaccca tctcctcgat caatcaggat   2400
ggcaagatgg agctgaggag ctcagcaaca tcaagtctgg agttggtctt taactcaact   2460
agctcgttta gacgtgtctg aacaccacat cacctgacag cacggggtgg tttcccagta   2520
aaatttacaa actcagctca agggcagctg tgttgctttc ctttccttga ctgctgagaa   2580
actttttgac agggaacaat ggaaacacac cttctgagct gaaacaaaca aacagaaaca   2640
```

-continued

```
aaacatacta accagcaaaa tccccaaatc atcaatcttg ggttctcttg aagggcagga   2700
gtgtgtttta tcttctcccg tcggagcaaa cactatagat gtcctcccta aaattctgtc   2760
ttccctagag cagccttgta aattagctag ggtcctaggg ttgaggccta aatcaactta   2820
aaattgtctc taaatatgta cctggatgtg tttgtacttg cagagcatgc cctcttcatg   2880
tgcctagggc tagtaactcc ctgtggcaga ggcatgtaaa gtattctgac tttttttttt   2940
tcaacttaat tccatttcca atgaaatgga tttttaaaaa ttttctccag agtgtgccat   3000
acttctccag ctattatagt taatgtgtgt gtatccttgt gtatatgtgt gtttgtgtgt   3060
gcatatgtgt tttcctagtg gttacatgct tactaggcaa ttatgtaaat aagcacagat   3120
tcataggcca gctaggcctg aggaaagaag acattataaa gggagggagt attttaacat   3180
tagctaaagc tatcacacaa ggcacccatt ctgctcccct caacagccac agcccacttc   3240
gtccttgtct taccaataag gggaaaggct ggaggtgata tttttcacag aaccgcagag   3300
gttttgaaca tatttgcaac attactttga gtacacatga gcaaaaaattc tgaattacat   3360
ccaggacccc agaagctcat tagatcaaag agtgcggggc ccctcagagt taccagagat   3420
tatctgcaga cttcagtgca atcgaatgac catggtccat tttgatggtc agaggtagga   3480
ctgaaaaacg ggtagaaaca attgctttag cgcttccttc tgtactttgc ctattaatgt   3540
tttgtctttc aaaaatatat tttctcctaa ttgtttaatt ggccaaataa tggctgcttt   3600
gggagttgtt tgtatgcctt ggaaggccat ggcctgcact ttaaaaataa gctaagtcca   3660
ttctgcccag cacgagcatt aggacagaga atgcacttat tttaggatcc ttaaaaattg   3720
cttcttttat ggcacactgg gttgacgact catctcgtgg gagccttcat ggcacattgc   3780
tgctgttctg caggtcccaa tacaattcct tccccctctc agtgccacgg cccccccatt   3840
gctagctaca caatttgata tcatattccc ttttcaactc caaaggagat gataagaagc   3900
tatcaaataa tgctttaaaa aagcaacttg agtttcttaa aagaaaggaa atgaatacat   3960
gctgcataat tacatttaaa atgtaagcca tgttattata agccgcactg agatgaagat   4020
ttgttagcaa accagtttca agcacactca cagtgaagta aaatcatgtt tttagcatct   4080
gaccattggg taatattatt ctttgttatc aaaagagaaa tatcacccaa gtatagtata   4140
cttagacctc ctagaggaaa cactccagtc ctaagcttgg tgtctgaaaa gaaaaacaaa   4200
aataaagatt atggatttag gtcagggaga cagagtgata ttctgaagac tgtgtttact   4260
ccctcatcat cggccaacca agatggagtt ctgcatcctg cacatatcag acatttcagt   4320
ccaatttcac caaagcatca gtgatgttct agaagcatcc cagcagatgg aggatcctaa   4380
tgtatttgtt ctgggtattt cccaaggccc agcctgactg gagtgtgtgt accaacagga   4440
tgaatccaat caagctacgc ccccatttg gtttcggatt ggccactctt gcatgtgcta   4500
gtagattgtg gaccaggacc agctgagcaa acacagttgc agagtagcct cctatgttgc   4560
taagaagctc ctgctaccca ggtgctttga acaattgagt gctccctctg gttaagtaga   4620
gatggcacca ccggagtttt tcttggatgt gaggctcaat cctttacggc agctattata   4680
acaaagtgaa ggttttctcc ctgggaaatg cagcttttct ctgtctttac taattctgcc   4740
agcctgtgag agtaaccacc gtagctgggc ttcttctcag attaattgtc atgccaggtc   4800
tccttcctgg ggagctgtga tgctgctctg aggttgattg ctgaggttgt agtgggtttt   4860
tgtttgtttt tgtttagttt ttcttgattg ttcttctttc tcttgaatgg caagagaaga   4920
aacactttct ctaacccacg gccaggaagg aaatggggag agagctactt cttagttcaa   4980
cctggttgcc acataaagga atctctctcc ttggactcag cccctaactg gaagcaagag   5040
```

-continued ccactgccct ctgagactga gagagcagcc cgaggaggag atgaatccat tctgcccttt 5100
gtttgggttt gcttcctgtc agtgagagaa tgctgaggca gttcctgtta tgtgaaactt 5160
tcatttttaa aaccaggaca gtcctaaaca gactggaatg agttggtcaa tcccagttgg 5220
tataggccca atgatttttg ctagtaagat aggattgtct tcctcaccca aaatgccttc 5280
aagtgcccta aaatgggtat tttaaaataa gaataaataa tgtagattta gtagaaaacc 5340
tggaaaacat aagaaacaaa gatgaaacga aaagtcccat gtaattccac cagttagagt 5400
taaccactga tatcgtttgg atatatggct ttctagtctt gtggatatcc ttttaatctc 5460
ttgtaatata aagtctgacc atatgtgtcc ttgcatttgt ttgtactgga ctctgttaat 5520
atttctatag taatggctca ctttggggag attgtgctgc acagtgtgta ggaagcacat 5580
tgggtgtatt attcccagtt ttgtattttg tatttccttg gagatgtgca ggggttaaga 5640
gcgggggtct ggccatagct ggccacgtca gactctcata tggtaagtat cacagagcac 5700
atgaggcctg tgttatgcgc tggaaagact caggaaatga gaggctctct tgttctgaca 5760
aggcaggctg agagctctca tttagggtca tcactccaga taactccaaa tgcagtttat 5820
tgctcaactg aagcagatga tcactttttg cctccaagtt cttcacccta gctagctcct 5880
ttcaaagagc cgagtatgct ggatcttaaa gggccaaact agttacatct catacatttc 5940
ctgatgttta gggatgcctt cacttccatc aaggatacct tggctgtgca aggacctctg 6000
atagctggag tctccttttg gtcactccca gctttgctta aacttgatgg agtttgctgt 6060
ccagtgatcc ccggatcttt catcatgaaa gccttccttc ctctcctgat gtctcaggcc 6120
tctagaccta gactggggtt ctggcaagga ggcctctatc aatagtatga catccaataa 6180
tatgttagtg ttgatatttt gcacagtaat attaagttta agagattata aaaatgagtt 6240
caaatgaata agttcctgtg atgtaagaga ttagatatgt gtgatttcag aaccaaagcc 6300 agggggggaat cccagaaaga aaacaataat ataatcctag tttctatata ttatttttat 6360
tcattactgt atatgggtag agatcaatat tctttcttat gctgttacta ttaattaaca 6420 catttttttaa ccatgccatt gaacttttgg gtgcattaaa gtggaaccca agctcctcat 6480
tagataataa tggcatttgg actgagtgcc atattcctaa atttccaata aagtggttga 6540
tatagagagg acaggataaa gccctatagt gtgcagttat atcaaaacag ctagtctcca 6600
ctttagggaa tgcctttact agagattaca tgaaatgtct gcttataaaa taagcagaga 6660
tggtaccact aagcagccac ctgaattgtt ttcctacagg aatgattact tttcagatcc 6720
atttatgttt tcatgctcaa tacttactcc ccttccctgc aacacccaaa gagtttactt 6780
ttgcaagtca tttggtcttc agtctactac tgaggaatag agaggcacta actgctttac 6840
ccaggatcag aactcatgtt cttaccttct attaatagag tacttgagcc agatggacta 6900
actggtctca cattttctct atcttggttt tacttccata aacatcaata tctttaccca 6960
catgattttt ccatcctccc atttttttcc atatgtatta gggttcagga actatgatgc 7020
taatgatcac atttcttcct agttcctaat ttcattagtg ccatttcctg atatctacag 7080
aaacaattat caatacatgt agctgcttga gccttattta gaaggctagc ctttcttttc 7140
caagtgctgt cagaatgtat acatttagtc tgtctttttc ccttttagga gtctttgttc 7200
tgggttgatg gcaaaattcc tctttttaca tgtgagattt ttgatttcac tgaattctac 7260
ctagattttt atggacattg gattttaaag aggaaaacac tcattttctt agtaagatat 7320
tggtgataca tagctatgcc attgatttcc atactcctga gctttgggga gggagacagt 7380

-continued

```
ggccaagtag caggcagaat aagatcatca ctcatgtcct gaatcaatca cactttcctt   7440

ctcggattgt gtatatgctc tgccacttcc tacatattac atcctgagtt tttaagtaaa   7500

gtggatctta gccagatttg agtctaatgg ctgattcatc ggcatagttc ttggcgttaa   7560

catctcagtg tcctctttag ttctctttga ggattcatgt cattgagggc ctttgtgcct   7620

ccacttgtct cagtatgagg aagaactttg gtgtgagggc ggagctatgt gaagggttgc   7680

tgggttgggg gattagttca tatggtcccc atgccatcta tttacttttg gagagagggg   7740

actttgagtg ggtgggtatg gatagatgtt cctcaaggaa accctgctgg ctaatgggca   7800

ctacatctgt gtattactgt gattctctct gtaagctccc catgtggcca aggaccccccc  7860

tcctaccagg gcacttcctg ccacctcatt gcactggtct caaccattca gcctgctgct   7920

gctgcaccat gttgggctgc ggtaggatag ggaaggggtt ctgttgattg ctaaatgttg   7980

cctaacttta tttccctctc ccacatttca tgcaagggag cggacctaac acatgacttg   8040

cattctcttc ctatgttcag aaactccagg gcttgcccac gtgtatgtat gagtgaccaa   8100

tggagcttgg aattctttat ctatatgatc tgtccgaaaa tgagatcttt tgtactggaa   8160

tttgtgatgt agttgatcat tcagagccaa acgcatatac caataaagac aagactgtca   8220

tataaaaaaa aaaaaaaaaa                                               8240
```

<210> SEQ ID NO 8
<211> LENGTH: 553
<212> TYPE: PRT
<213> ORGANISM: Homo sapiens
<300> PUBLICATION INFORMATION:
<308> DATABASE ACCESSION NUMBER: NCBI/AF410901
<309> DATABASE ENTRY DATE: 2002-01-25

<400> SEQUENCE: 8

```
Met Ser Ser Trp Ile Arg Trp His Gly Pro Ala Met Ala Arg Leu Trp
 1               5                  10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205
```

-continued

```
Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
    450                 455                 460

Lys Asp Phe Ser Trp Phe Gly Phe Gly Lys Val Lys Ser Arg Gln Gly
465                 470                 475                 480

Val Gly Pro Ala Ser Val Ile Ser Asn Asp Asp Asp Ser Ala Ser Pro
                485                 490                 495

Leu His His Ile Ser Asn Gly Ser Asn Thr Pro Ser Ser Ser Glu Gly
            500                 505                 510

Gly Pro Asp Ala Val Ile Ile Gly Met Thr Lys Ile Pro Val Ile Glu
        515                 520                 525

Asn Pro Gln Tyr Phe Gly Ile Thr Asn Ser Gln Leu Lys Pro Asp Thr
    530                 535                 540

Trp Pro Arg Gly Ser Pro Lys Thr Ala
545                 550
```

<210> SEQ ID NO 9
<211> LENGTH: 4351
<212> TYPE: DNA
<213> ORGANISM: Mus musculus
<300> PUBLICATION INFORMATION:
<308> DATABASE ACCESSION NUMBER: NCBI/X17647
<309> DATABASE ENTRY DATE: 1995-03-22
<313> RELEVANT RESIDUES: (1)..(4351)

<400> SEQUENCE: 9

-continued

```
aggctgcggc ggcggcgcgc cgttagagcc cagtcgctgc ttcagctgct gttgctgctt    60
ctgccaggct ctgctccctg cgcttgctac gggaggccgg ggaagccgcg cggacagtcc   120
tcggtggcct gggccggcac tgtcctgcta ccgcagttgc tccccagccc tgaggtgcgc   180
accgatatcg atattcgtgc cggtttagcg gttctgcgac ccaaagagtc cagggagatc   240
caccgagtgg tgcctggtgt ataggactat gcagccgcct tgtggctcgg agcagcggcc   300
cgcgatgtcc cagccactgt gaaccatttg gtcagcgcca acctgctcag ccccagcacc   360
gacaggctca gcctctggta cgctccactc cgcgggaggc caccagcacc aagcagcaag   420
agggcgcagg gaaggcctcc cccctccggc gggggacgcc tggctcagcg tagggacacg   480
cactccgact gactggcact ggcagctcgg gatgtcgccc tggctgaagt ggcatggacc   540
cgccatggcg cggctctggg gcttatgcct gctggtcttg ggcttctgga gggcctctct   600
cgcctgcccg acgtcctgca aatgcagttc cgctaggatt tggtgtactg agccttctcc   660
aggcatcgtg gcattcccga ggttggaacc taacagcgtt gacccggaga acatcacgga   720
aattctcatt gcaaaccaga aaaggctaga aatcatcaat gaagatgacg ttgaagctta   780
cgtggggctg agaaacctta caattgtgga ttccggctta aagtttgtgg cttacaaagc   840
gtttctgaaa aacagcaacc tgcggcacat aaatttcaca cgaaacaagc tgacgagttt   900
gtccaggaga catttccgcc accttgactt gtctgacctg atcctgacgg gtaatccgtt   960
cacgtgctcc tgcgacatca tgtggctcaa gactctccag gagactaaat ccagccccga  1020
cactcaggat ttgtactgcc tcaatgagag cagcaagaac atgcccctgg cgaacctgca  1080
gatacccaat tgtggtctgc catctgcacg tctggctgct cctaacctca ccgtggagga  1140
aggaaagtct gtgacccttt cctgcagtgt gggggggtgac ccactcccca ccttgtactg  1200
ggacgttggg aatttggttt ccaagcacat gaatgaaaca agccacacac agggctcctt  1260
aaggataacg aacatttcat ctgatgacag tggaaagcaa atctcttgtg tggcagaaaa  1320
ccttgtagga gaagatcaag attctgtgaa cctcactgtg cattttgcgc caactatcac  1380
gtttctcgag tctccaacct cagatcacca ctggtgcatt ccattcactg tgagaggcaa  1440
ccccaagcct gcgcttcagt ggttctacaa tggggccata ctgaatgagt ccaagtacat  1500
ctgtactaag atccacgtca ccaatcacac ggagtaccat ggctgcctcc agctggataa  1560
ccccactcat atgaataacg gagactacac cctgatggcc aagaacgagt atgggaagga  1620
tgagagacag atctccgctc acttcatggg ccggcctgga gtcgactacg agacaaaccc  1680
aaattaccct gaagtcctct atgaagactg gaccacgcca actgacattg gggatactac  1740
gaacaaaagt aatgaaatcc cctccacgga tgttgctgac caaagcaatc gggagcatct  1800
ctcggtctat gccgtggtgg tgattgcatc tgtggtggga ttctgcctgc tggtgatgtt  1860
gctcctgctc aagttggcga gacattccaa gtttggcatg aaaggcccag cttcggtcat  1920
cagcaacgac gatgactctg ccagccccct ccaccacatc tccaatggga gtaacactcc  1980
atcttcttcg gagggcggtc ccgacgctgt cattattgga atgaccaaga ttcctgttat  2040
tgaaaacccc cagtactttg gcatcaccaa cagtcagctc aagccagaca catttgttca  2100
gcacatcaag agacacaaca tcgttctgaa gagggaactt ggggaaggag ccttcgggaa  2160
agttttcctt gccgagtgct acaacctctg cccagagcag gataagatcc tggtggctgt  2220
gaagacgctg aaggacgcca gcgacaatgc acgcaaggac tttcatcggg aagctgagct  2280
gctgaccaac ctccagcacg agcacattgt caagttctac ggtgtctgtg tggagggcga  2340
cccactcatc atggtctttg agtacatgaa gcacggggac ctcaacaagt tccttagggc  2400
```

-continued

```
acacgggccc gacgcagtgc tgatggcaga gggtaacccg cccacagagc tgacgcagtc   2460
gcagatgctg cacatcgctc agcaaatcgc agcaggtatg gtctacctgg cgtcccaaca   2520
ctttgtgcac cgtgacctgg ccacccggaa ctgcctggtg ggagagaacc tgctggtgaa   2580
aattggggac tttgggatgt cccgagatgt gtacagcacc gactactatc gggtcggtgg   2640
ccacacaatg ttgcccatcc gatggatgcc tccagagagc atcatgtata ggaaattcac   2700
caccgagagc gacgtctgga gcctgggcgt tgtgttgtgg gagatcttca cctacggcaa   2760
gcagccctgg tatcagctat cgaacaatga ggtgatagag tgcatcaccc agggaagagt   2820
ccttcagcgg cctcgaacct gtccccagga ggtgtatgag ctcatgctcg gatgctggca   2880
gcgggaacca cacacccgga agaacatcaa gagcatccac accctccttc agaacttggc   2940
caaggcatct cccgtctacc tggatatcct aggctagggt cctccttctg cccagaccgt   3000
ccttcccaag gccctcctca gactggtcct cagactggcc tacacgacga acctcttgac   3060
tgccgctgac gtcatgacct tgctgtcctt cgctctgaca gagttgacag gaccaggagc   3120
ggctctctgg gggaggcagt gtgtgcttct ccatccacag acagtattaa ctcgcttctg   3180
gcatcgtctc tttctctccc ttgggtttgt ttctttcttt tgccccttcc ccttttatca   3240
ttatttattc atttatttat tttctggtct tcacgcttca cggccctcag tctctccttg   3300
accaatctgg cttctgcatt cctattaact gtacatagac aaaggcctta acaaacctaa   3360
tttgttatat cagcagacac tccagtttgc ccaccacaac taacaatgcc ttgttgtatt   3420
cctgcctttg acgtggatga aaaaaagaga aaaaaggccg agactctcct gcaggaatcg   3480
gatgaggcct ctgagctcaa gcccgtggaa ctggacactt ttgaaggaaa catcacaaag   3540
caactggtga agaggctcac ctcggctgag gggcccgtca ctactgacaa gcttttcttt   3600
gaaggctctg ttggtagcga gtctgaggct ggccggtcct ttctggatgg cagcctggaa   3660
gatgccttca atggactctt ccttgcatta gacccacaca agaagcagta caaagagttc   3720
caggatctga accaagaagt cactcacttg gatgatgttc tcaaagatgc taaacatctt   3780
gaggatcaga gactcaatga tgctgcttcc cggatggaga tcacagaggg tgaatgagac   3840
aaccgagatt taaaagactg aaggacattt tcccatgtgc ttctgtgtca tcccaagtgt   3900
ctgggacaga tccccgcaag gcccttccta ccttgtgcta agagtctgca aggggatcct   3960
cctagccaga cagaggacac gcaggtgtct cctttgcaag atttgtcctg ttcaacctac   4020
ctcacgtcct cttgaatatg tggatatgct tttctttctc caggctaaag cactggcata   4080
gcagccacat agcaggcttc tgtgttggct catgtcctgc aaacctgctg tagaaggaac   4140
ttgtccccat aattccaggg cttgcccgag gggtgatggg acttgtgcct ttcaccttca   4200
ggggagtcgg gatcattgtc ccatcatgcc caagtcaccc atttgcctct ccgtgctcag   4260
aaaaaaaagc atccttgaat ggaacatggt gatgcagggc tccgtgccaa agcagcctag   4320
ggcaggtgta tttgagcagt ttccttttct g                                  4351
```

<210> SEQ ID NO 10
<211> LENGTH: 821
<212> TYPE: PRT
<213> ORGANISM: Mus musculus
<300> PUBLICATION INFORMATION:
<308> DATABASE ACCESSION NUMBER: NCBI/X17647
<309> DATABASE ENTRY DATE: 1995-03-22
<313> RELEVANT RESIDUES: (1)..(821)

<400> SEQUENCE: 10

-continued

```
Met Ser Pro Trp Leu Lys Trp His Gly Pro Ala Met Ala Arg Leu Trp
 1               5                  10                  15

Gly Leu Cys Leu Leu Val Leu Gly Phe Trp Arg Ala Ser Leu Ala Cys
            20                  25                  30

Pro Thr Ser Cys Lys Cys Ser Ser Ala Arg Ile Trp Cys Thr Glu Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Leu Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala Tyr Lys Ala Phe Leu
            100                 105                 110

Lys Asn Ser Asn Leu Arg His Ile Asn Phe Thr Arg Asn Lys Leu Thr
        115                 120                 125

Ser Leu Ser Arg Arg His Phe Arg His Leu Asp Leu Ser Asp Leu Ile
    130                 135                 140

Leu Thr Gly Asn Pro Phe Thr Cys Ser Cys Asp Ile Met Trp Leu Lys
145                 150                 155                 160

Thr Leu Gln Glu Thr Lys Ser Ser Pro Asp Thr Gln Asp Leu Tyr Cys
                165                 170                 175

Leu Asn Glu Ser Ser Lys Asn Met Pro Leu Ala Asn Leu Gln Ile Pro
            180                 185                 190

Asn Cys Gly Leu Pro Ser Ala Arg Leu Ala Ala Pro Asn Leu Thr Val
        195                 200                 205

Glu Glu Gly Lys Ser Val Thr Leu Ser Cys Ser Val Gly Gly Asp Pro
    210                 215                 220

Leu Pro Thr Leu Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Arg Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Met Ala Lys Asn Glu Tyr Gly
        355                 360                 365

Lys Asp Glu Arg Gln Ile Ser Ala His Phe Met Gly Arg Pro Gly Val
    370                 375                 380

Asp Tyr Glu Thr Asn Pro Asn Tyr Pro Glu Val Leu Tyr Glu Asp Trp
385                 390                 395                 400

Thr Thr Pro Thr Asp Ile Gly Asp Thr Thr Asn Lys Ser Asn Glu Ile
                405                 410                 415

Pro Ser Thr Asp Val Ala Asp Gln Ser Asn Arg Glu His Leu Ser Val
```

-continued

```
            420                 425                 430

Tyr Ala Val Val Val Ile Ala Ser Val Val Gly Phe Cys Leu Leu Val
        435                 440                 445

Met Leu Leu Leu Leu Lys Leu Ala Arg His Ser Lys Phe Gly Met Lys
    450                 455                 460

Gly Pro Ala Ser Val Ile Ser Asn Asp Asp Asp Ser Ala Ser Pro Leu
465                 470                 475                 480

His His Ile Ser Asn Gly Ser Asn Thr Pro Ser Ser Ser Glu Gly Gly
                485                 490                 495

Pro Asp Ala Val Ile Ile Gly Met Thr Lys Ile Pro Val Ile Glu Asn
            500                 505                 510

Pro Gln Tyr Phe Gly Ile Thr Asn Ser Gln Leu Lys Pro Asp Thr Phe
        515                 520                 525

Val Gln His Ile Lys Arg His Asn Ile Val Leu Lys Arg Glu Leu Gly
    530                 535                 540

Glu Gly Ala Phe Gly Lys Val Phe Leu Ala Glu Cys Tyr Asn Leu Cys
545                 550                 555                 560

Pro Glu Gln Asp Lys Ile Leu Val Ala Val Lys Thr Leu Lys Asp Ala
                565                 570                 575

Ser Asp Asn Ala Arg Lys Asp Phe His Arg Glu Ala Glu Leu Leu Thr
            580                 585                 590

Asn Leu Gln His Glu His Ile Val Lys Phe Tyr Gly Val Cys Val Glu
        595                 600                 605

Gly Asp Pro Leu Ile Met Val Phe Glu Tyr Met Lys His Gly Asp Leu
    610                 615                 620

Asn Lys Phe Leu Arg Ala His Gly Pro Asp Ala Val Leu Met Ala Glu
625                 630                 635                 640

Gly Asn Pro Pro Thr Glu Leu Thr Gln Ser Gln Met Leu His Ile Ala
                645                 650                 655

Gln Gln Ile Ala Ala Gly Met Val Tyr Leu Ala Ser Gln His Phe Val
            660                 665                 670

His Arg Asp Leu Ala Thr Arg Asn Cys Leu Val Gly Glu Asn Leu Leu
        675                 680                 685

Val Lys Ile Gly Asp Phe Gly Met Ser Arg Asp Val Tyr Ser Thr Asp
    690                 695                 700

Tyr Tyr Arg Val Gly Gly His Thr Met Leu Pro Ile Arg Trp Met Pro
705                 710                 715                 720

Pro Glu Ser Ile Met Tyr Arg Lys Phe Thr Thr Glu Ser Asp Val Trp
                725                 730                 735

Ser Leu Gly Val Val Leu Trp Glu Ile Phe Thr Tyr Gly Lys Gln Pro
            740                 745                 750

Trp Tyr Gln Leu Ser Asn Asn Glu Val Ile Glu Cys Ile Thr Gln Gly
        755                 760                 765

Arg Val Leu Gln Arg Pro Arg Thr Cys Pro Gln Glu Val Tyr Glu Leu
    770                 775                 780

Met Leu Gly Cys Trp Gln Arg Glu Pro His Thr Arg Lys Asn Ile Lys
785                 790                 795                 800

Ser Ile His Thr Leu Leu Gln Asn Leu Ala Lys Ala Ser Pro Val Tyr
                805                 810                 815

Leu Asp Ile Leu Gly
            820
```

<210> SEQ ID NO 11

-continued

<211> LENGTH: 2484
<212> TYPE: DNA
<213> ORGANISM: Mus musculus
<300> PUBLICATION INFORMATION:
<308> DATABASE ACCESSION NUMBER: NCBI/M33385
<309> DATABASE ENTRY DATE: 1993-04-23
<313> RELEVANT RESIDUES: (1)..(2484)

<400> SEQUENCE: 11
atgtcgccct ggctgaagtg gcatggaccc gccatggcgc ggctctgggg cttatgcctg 60
ctggtcttgg gcttctggag ggcctctctc gcctgcccga cgtcctgcaa atgcagttcc 120
gctaggattt ggtgtactga gccttctcca ggcatcgtgg cattcccgag gttggaacct 180
aacagcgttg acccggagaa catcacggaa attctcattg caaaccagaa aaggctagaa 240
atcatcaatg aagatgacgt tgaagcttac gtggggctga gaaaccttac aattgtggat 300
tccggcttaa agtttgtggc ttacaaagcg tttctgaaaa acagcaacct gcggcacata 360
aatttcacac gaaacaagct gacgagtttg tccaggagac atttccgcca ccttgacttg 420
tctgacctga tcctgacggg taatccgttc acgtgctcct gcgacatcat gtggctcaag 480
actctccagg agactaaatc cagccccgac actcaggatt tgtactgcct caatgagagc 540
agcaagaaca tgcccctggc gaacctgcag atacccaatt gtggtctgcc atctgcacgt 600
ctggctgctc ctaacctcac cgtggaggaa ggaaagtctg tgaccctttc ctgcagtgtg 660
gggggtgacc cactccccac cttgtactgg gacgttggga atttggtttc caagcacatg 720
aatgaaacaa gccacacaca gggctcctta aggataacga acatttcatc tgatgacagt 780
ggaaagcaaa tctcttgtgt ggcagaaaac cttgtaggag aagatcaaga ttctgtgaac 840
ctcactgtgc attttgcgcc aactatcacg tttctcgagt ctccaacctc agatcaccac 900
tggtgcattc cattcactgt gagaggcaac cccaagcctg cgcttcagtg gttctacaat 960
ggggccatac tgaatgagtc caagtacatc tgtactaaga tccacgtcac caatcacacg 1020
gagtaccatg gctgcctcca gctggataac cccactcata tgaataacgg agactacacc 1080
ctgatggcca agaacgagta tgggaaggat gagagacaga tctccgctca cttcatgggc 1140
cggcctggag tcgactacga gacaaaccca aattaccctg aagtcctcta tgaagactgg 1200
accacgccaa ctgacattgg ggatactacg aacaaaagta atgaaatccc ctccacggat 1260
gttgctgacc aaagcaatcg ggagcatctc tcggtctatg ccgtggtggt gattgcatct 1320
gtggtgggat tctgcctgct ggtgatgttg ctcctgctca agttggcgag acattccaag 1380
tttggcatga aggttttgt tttgtttcat aagatcccac tggatgggta gctgagataa 1440
aggaaagaca aaggctgggg ctgtggtgct tgttgcctga cgccctgtga gctgaactct 1500
gggactgctg ttgcctatcc caggaagtgc tgcttatttg agggtgtctg gtggaaatgg 1560
gtaatctccg aggatgtctg cagcctgctt gttgtgagct gtgactgggg aaccccaagg 1620
cagaggcagg ggtcaggcag ctgagaagca gcagaagaac acacttagat tcaccttctg 1680
ttcttacaat agttcaaata tagaatcgaa gtgaaatctc attggattat gcctctctaa 1740
tgaaaagcga gctgtttgac tatacggaaa atgtgctgac attaattgct tctgtttatt 1800
aaaggtgatt tgcaaattaa aaactctgca tctatcatct atccatctat ctgtttgtct 1860
atcatatcta tctgtctgtc tatctgtcta tcatctatct acctacctct ctatcatatc 1920
tatctgtctg tctatctatc tatctatcta tctatctatc tatctatcta tctatctatc 1980
tatctatcat ctatctacct atcatcgatc tacttatcta tcatctatct atctacctat 2040
catcgattta cttatctatc atctatctat ctatctatct atctatctat ctatctatct 2100

-continued

```
atctgtcatc tatctaaagt catagctagg tctaagtgca cactaaaagt ctaatccaca   2160

cataacacct atttcagcaa catcttctgt tctctaacct ttgctaactt ctgtgatttc   2220

cacctacaac cctgcgactg atagacttaa aggcacattg gtggtgtcat tagtaggttc   2280

tttgttttgc tggcagcaaa gacccaaact cttcgctaac gattgctttc aaagtccacc   2340

cggcaggtag aacggagcag caccagggac tgtgtggcca ggagtatgga cctgaattaa   2400

ccacagcctg agaataaata atggtagggt atatgcatat agggaattaa aatcttgtcc   2460

ctttccattg ccctctgcta accg                                          2484
```

```
<210> SEQ ID NO 12
<211> LENGTH: 476
<212> TYPE: PRT
<213> ORGANISM: Mus musculus
<300> PUBLICATION INFORMATION:
<308> DATABASE ACCESSION NUMBER: NCBI/M33385
<309> DATABASE ENTRY DATE: 1993-04-27
<313> RELEVANT RESIDUES: (1)..(476)

<400> SEQUENCE: 12

Met Ser Pro Trp Leu Lys Trp His Gly Pro Ala Met Ala Arg Leu Trp
 1               5                  10                  15

Gly Leu Cys Leu Leu Val Leu Gly Phe Trp Arg Ala Ser Leu Ala Cys
            20                  25                  30

Pro Thr Ser Cys Lys Cys Ser Ser Ala Arg Ile Trp Cys Thr Glu Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Leu Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala Tyr Lys Ala Phe Leu
            100                 105                 110

Lys Asn Ser Asn Leu Arg His Ile Asn Phe Thr Arg Asn Lys Leu Thr
        115                 120                 125

Ser Leu Ser Arg Arg His Phe Arg His Leu Asp Leu Ser Asp Leu Ile
    130                 135                 140

Leu Thr Gly Asn Pro Phe Thr Cys Ser Cys Asp Ile Met Trp Leu Lys
145                 150                 155                 160

Thr Leu Gln Glu Thr Lys Ser Ser Pro Asp Thr Gln Asp Leu Tyr Cys
                165                 170                 175

Leu Asn Glu Ser Ser Lys Asn Met Pro Leu Ala Asn Leu Gln Ile Pro
            180                 185                 190

Asn Cys Gly Leu Pro Ser Ala Arg Leu Ala Ala Pro Asn Leu Thr Val
        195                 200                 205

Glu Glu Gly Lys Ser Val Thr Leu Ser Cys Ser Val Gly Gly Asp Pro
    210                 215                 220

Leu Pro Thr Leu Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
```

-continued

```
        275                 280                 285

Ile Thr Phe Leu Glu Ser Pro Thr Ser Asp His His Trp Cys Ile Pro
    290                 295                 300

Phe Thr Val Arg Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Met Ala Lys Asn Glu Tyr Gly
        355                 360                 365

Lys Asp Glu Arg Gln Ile Ser Ala His Phe Met Gly Arg Pro Gly Val
    370                 375                 380

Asp Tyr Glu Thr Asn Pro Asn Tyr Pro Glu Val Leu Tyr Glu Asp Trp
385                 390                 395                 400

Thr Thr Pro Thr Asp Ile Gly Asp Thr Thr Asn Lys Ser Asn Glu Ile
                405                 410                 415

Pro Ser Thr Asp Val Ala Asp Gln Ser Asn Arg Glu His Leu Ser Val
            420                 425                 430

Tyr Ala Val Val Val Ile Ala Ser Val Val Gly Phe Cys Leu Leu Val
        435                 440                 445

Met Leu Leu Leu Leu Lys Leu Ala Arg His Ser Lys Phe Gly Met Lys
    450                 455                 460

Gly Phe Val Leu Phe His Lys Ile Pro Leu Asp Gly
465                 470                 475
```

<210> SEQ ID NO 13
<211> LENGTH: 2838
<212> TYPE: DNA
<213> ORGANISM: Homo sapiens
<300> PUBLICATION INFORMATION:
<308> DATABASE ACCESSION NUMBER: NCBI/XM_038336
<309> DATABASE ENTRY DATE: 2002-02-07

<400> SEQUENCE: 13

```
cgagccggcc accatgcccg gcagaccgcg ccactaggcg ctcctcgcgg ctcccacccg      60

gcggcggcgg cggcggcggc ggcgtccgcg atggtttcag acgctgaagg attttgcatc     120

tgatcgctcg gcgtttcaaa gaagcagcga tcggagatgg atgtctctct ttgcccagcc     180

aagtgtagtt tctggcggat tttcttgctg ggaagcgtct ggctggacta tgtgggctcc     240

gtgctggctt gccctgcaaa ttgtgtctgc agcaagactg agatcaattg ccggcggccg     300

gacgatggga acctcttccc cctcctggaa gggcaggatt cagggaacag caatgggaac     360

gccagtatca acatcacgga catctcaagg aatatcactt ccatacacat agagaactgg     420

cgcagtcttc acacgctcaa cgccgtggac atggagctct acaccggact tcaaaagctg     480

accatcaaga actcaggact tcggagcatt cagcccagag cctttgccaa gaacccccat     540

ttgcgttata taaacctgtc aagtaaccgg ctcaccacac tctcgtggca gctcttccag     600

acgctgagtc ttcgggaatt gcagttggag cagaactttt tcaactgcag ctgtgacatc     660

cgctggatgc agctctggca ggagcagggg gaggccaagc tcaacagcca gaacctctac     720

tgcatcaacg ctgatggctc ccagcttcct ctcttccgca tgaacatcag tcagtgtgac     780

cttcctgaga tcagcgtgag ccacgtcaac ctgaccgtac gagagggtga caacgctgtt     840

atcacttgca atggctctgg atcacccctt cctgatgtgg actggatagt cactgggctg     900
```

-continued

```
cagtccatca acactcacca gaccaatctg aactggacca atgttcatgc catcaacttg    960

acgctggtga atgtgacgag tgaggacaat ggcttcaccc tgacgtgcat tgcagagaac   1020

gtggtgggca tgagcaatgc cagtgttgcc ctcactgtct actatccccc acgtgtggtg   1080

agcctggagg agcctgagct gcgcctggag cactgcatcg agtttgtggt gcgtggcaac   1140

cccccaccaa cgctgcactg gctgcacaat gggcagcctc tgcgggagtc caagatcatc   1200

catgtggaat actaccaaga gggagagatt tccgagggct gcctgctctt caacaagccc   1260

acccactaca acaatggcaa ctataccctc attgccaaaa acccactggg cacagccaac   1320

cagaccatca atggccactt cctcaaggag ccctttccag agagcacgga taactttatc   1380

ttgtttgacg aagtgagtcc cacacctcct atcactgtga cccacaaacc agaagaagac   1440

acttttgggg tatccatagc agttggactt gctgcttttg cctgtgtcct gttggtggtt   1500

ctcttcgtca tgatcaacaa atatggtcga cggtccaaat ttggaatgaa gggtcccgtg   1560

gctgtcatca gtggtgagga ggactcagcc agcccactgc accacatcaa ccacggcatc   1620

accacgccct cgtcactgga tgccgggccc gacactgtgg tcattggcat gactcgcatc   1680

cctgtcattg agaaccccca gtacttccgt cagggacaca actgccacaa gccggacacg   1740

tatgtgcagc acattaagag gagagacatc gtgctgaagc gagaactggg tgagggagcc   1800

tttggaaagg tcttcctggc cgagtgctac aacctcagcc cgaccaagga caagatgctt   1860

gtggctgtga aggccctgaa ggatcccacc ctggctgccc ggaaggattt ccagagggag   1920

gccgagctgc tcaccaacct gcagcatgag cacattgtca agttctatgg agtgtgcggc   1980

gatggggacc ccctcatcat ggtctttgaa tacatgaagc atggagacct gaataagttc   2040

ctcagggccc atgggccaga tgcaatgatc cttgtggatg gacagccacg ccaggccaag   2100

ggtgagctgg ggctctccca aatgctccac attgccagtc agatcgcctc gggtatggtg   2160

tacctggcct cccagcactt tgtgcaccga gacctggcca ccaggaactg cctggttgga   2220

gcgaatctgc tagtgaagat tggggacttc ggcatgtcca gagatgtcta cagcacggat   2280

tattacaggc tctttaatcc atctggaaat gatttttgta tatggtgtga ggtgggagga   2340

cacaccatgc tccccattcg ctggatgcct cctgaaagca tcatgtaccg gaagttcact   2400

acagagagtg atgtatggag cttcggggtg atcctctggg agatcttcac ctatggaaag   2460

cagccatggt tccaactctc aaacacggag gtcattgagt gcattaccca aggtcgtgtt   2520

ttggagcggc cccgagtctg ccccaaagag gtgtacgatg tcatgctggg gtgctggcag   2580

agggaaccac agcagcggtt gaacatcaag gagatctaca aaatcctcca tgctttgggg   2640

aaggccaccc caatctacct ggacattctt ggctagtggt ggctggtggt catgaattca   2700

tactctgttg cctcctctct ccctgcctca catctccctt ccacctcaca actccttcca   2760

tccttgactg aagcgaacat cttcatataa actcaagtgc ctgctacaca tacaacactg   2820

aaaaaaggaa aaaaaaag                                                 2838


<210> SEQ ID NO 14
<211> LENGTH: 839
<212> TYPE: PRT
<213> ORGANISM: Homo sapiens
<300> PUBLICATION INFORMATION:
<308> DATABASE ACCESSION NUMBER: NCBI/XM_038336
<309> DATABASE ENTRY DATE: 2002-02-07

<400> SEQUENCE: 14

Met Asp Val Ser Leu Cys Pro Ala Lys Cys Ser Phe Trp Arg Ile Phe
 1               5                  10                  15
```

-continued

```
Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
    130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
        195                 200                 205

Leu Pro Glu Ile Ser Val Ser His Val Asn Leu Thr Val Arg Glu Gly
    210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
        275                 280                 285

Val Val Gly Met Ser Asn Ala Ser Val Ala Leu Thr Val Tyr Tyr Pro
    290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Pro Thr Leu His Trp Leu
                325                 330                 335

His Asn Gly Gln Pro Leu Arg Glu Ser Lys Ile Ile His Val Glu Tyr
            340                 345                 350

Tyr Gln Glu Gly Glu Ile Ser Glu Gly Cys Leu Leu Phe Asn Lys Pro
        355                 360                 365

Thr His Tyr Asn Asn Gly Asn Tyr Thr Leu Ile Ala Lys Asn Pro Leu
    370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
                405                 410                 415

Pro Pro Ile Thr Val Thr His Lys Pro Glu Glu Asp Thr Phe Gly Val
            420                 425                 430
```

-continued

```
Ser Ile Ala Val Gly Leu Ala Ala Phe Ala Cys Val Leu Leu Val Val
        435                 440                 445

Leu Phe Val Met Ile Asn Lys Tyr Gly Arg Arg Ser Lys Phe Gly Met
    450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
        515                 520                 525

Tyr Val Gln His Ile Lys Arg Arg Asp Ile Val Leu Lys Arg Glu Leu
    530                 535                 540

Gly Glu Gly Ala Phe Gly Lys Val Phe Leu Ala Glu Cys Tyr Asn Leu
545                 550                 555                 560

Ser Pro Thr Lys Asp Lys Met Leu Val Ala Val Lys Ala Leu Lys Asp
                565                 570                 575

Pro Thr Leu Ala Ala Arg Lys Asp Phe Gln Arg Glu Ala Glu Leu Leu
            580                 585                 590

Thr Asn Leu Gln His Glu His Ile Val Lys Phe Tyr Gly Val Cys Gly
        595                 600                 605

Asp Gly Asp Pro Leu Ile Met Val Phe Glu Tyr Met Lys His Gly Asp
    610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
                645                 650                 655

Leu His Ile Ala Ser Gln Ile Ala Ser Gly Met Val Tyr Leu Ala Ser
            660                 665                 670

Gln His Phe Val His Arg Asp Leu Ala Thr Arg Asn Cys Leu Val Gly
        675                 680                 685

Ala Asn Leu Leu Val Lys Ile Gly Asp Phe Gly Met Ser Arg Asp Val
    690                 695                 700

Tyr Ser Thr Asp Tyr Tyr Arg Leu Phe Asn Pro Ser Gly Asn Asp Phe
705                 710                 715                 720

Cys Ile Trp Cys Glu Val Gly Gly His Thr Met Leu Pro Ile Arg Trp
                725                 730                 735

Met Pro Pro Glu Ser Ile Met Tyr Arg Lys Phe Thr Thr Glu Ser Asp
            740                 745                 750

Val Trp Ser Phe Gly Val Ile Leu Trp Glu Ile Phe Thr Tyr Gly Lys
        755                 760                 765

Gln Pro Trp Phe Gln Leu Ser Asn Thr Glu Val Ile Glu Cys Ile Thr
    770                 775                 780

Gln Gly Arg Val Leu Glu Arg Pro Arg Val Cys Pro Lys Glu Val Tyr
785                 790                 795                 800

Asp Val Met Leu Gly Cys Trp Gln Arg Glu Pro Gln Gln Arg Leu Asn
                805                 810                 815

Ile Lys Glu Ile Tyr Lys Ile Leu His Ala Leu Gly Lys Ala Thr Pro
            820                 825                 830

Ile Tyr Leu Asp Ile Leu Gly
        835
```

-continued

<210> SEQ ID NO 15
<211> LENGTH: 1030
<212> TYPE: DNA
<213> ORGANISM: Homo sapiens
<300> PUBLICATION INFORMATION:
<308> DATABASE ACCESSION NUMBER: NCBI/AJ224536
<309> DATABASE ENTRY DATE: 2000-11-29

<400> SEQUENCE: 15

```
ccgacacgga tctttccagg gcccacaaat gctgcatggt ctccaaagga gatttcatcc     60

tcagaagcta caatgatatc tctttataga agttgtagtc ttcaggtctt cagtgagcta    120

acagcttttg tttttccaat ggtttatgcc ctaacaatgg caaggaagat tttaaggaac    180

caaacaccac cacctcctct catctcctca tcatccccgc cttgtcacat tgctttcctc    240

ttgaaaatta gctgaatttt tttgatggga tattagaagc cagaaagagg gtcttgggtc    300

caggattatc tcccaagtca gaagaaacat ccatccaggc ccaggaatga cactctgaat    360

ggcaatgatg ggcaccattt tgagacattc tggtccaaga aggaaaatgg gggcaaatat    420

gttaggaaaa gtgcaggaca gagttcatgg tgatggtgaa tctttcttct ctgactctaa    480

cttgtgccat ttctataatg ccagggtgag attcttagga tctagatttt atgcgtaaaa    540

taaaccagct gccactacag gcacagcaga gtgggtacag gagctgagaa acctggattt    600

ctgtttctgg cattgtgcac ttaagaaaaa tactttccca tgttttttgc acttggggtt    660

taatactgac cattaattcc cccatgtctg cctcttctgc caggggtctt ttcaaacata    720

gacaatcatg ggatattaaa cttgaaggac aatagagatc atctagtccc atcaactcac    780

tatatatatg aggaacctga ggtccagagt ggggaagtgt cttacccaag gtcacatggt    840

gagttacctc ctttgacgtc tttgtatgca gtaaagatcc ctcccctaac caattttggt    900

tcttaagacc ttaagactca tcaagcctcc atatatttcg tggactgagg tacgactagg    960

tgcccagcac gggatttggt actaaaaaaa tcccttaaat taaaggagtg tcttccaggg   1020

gaggaagctt                                                          1030
```

<210> SEQ ID NO 16
<211> LENGTH: 1113
<212> TYPE: DNA
<213> ORGANISM: Homo sapiens
<300> PUBLICATION INFORMATION:
<308> DATABASE ACCESSION NUMBER: NCBI/AJ224537
<309> DATABASE ENTRY DATE: 2000-11-29

<400> SEQUENCE: 16

```
cagtggaggc tgcagcaaaa tggagtgttt ccagtttctc tgaccatgca gggttttaag     60

ttaatcccct cctcctatcc ttccctttttg ctgacagttc ttccccttttc aagctccctc    120

tctatttccc ctcctagttt tgatcttctt tgggggtttt ggtttttact ttattttgct    180

tttttctgtt tttttttctt tttgtttttt ataggtttca gagaaattat gttgaatcca    240

ataagccttc ccggacattc caagcctctt aaccatggca tctatgttga ggatgtcaat    300

gtttatttca gcaaaggacg tcatggcttt taaaaactcc ttttaagcct ccttgttttg    360

atgtcacctt ggtaggctgg gccctctgag aggttggaag ctctaggcat tgttctcttt    420

ggatccaggg atgctaagta gaaactgcat gagccaccag tgccccggca ccctttaaca    480

ccaccagatg ggtgttttcc cccatccacc actggcaggg ttgcccccttc cctccaatca    540

tcactgtgct cctttttttcc cggcctacga ggcagctcct gccactatct ttagagccaa    600

taaagagaat taaaaacctg tgcaccagga gcatctttta aatacactag ccattctctt    660
```

-continued

```
gctttacaaa aacaacctaa ccatcacaag aaagcctgat gaagtccagc cgtgctccag    720

cctcactttc cctgcttgga agcgtggggt ctccctggct ctcccaggat accatgctgt    780

cctcttagtg acctcgtcgc cctgcaacct ccagtgggga agagtcacag agagcaccta    840

agcagaggtg gagacggcgc ggtaagagga gggggagcca ggctcaagta ttggcaccaa    900

gttaggtctc agaggaaaga atggaaacca atcactttac atttttattt ttattttcgg    960

tggaaaaatc atcctttttt gggacatact tgccccctac ttcctcttct ctctggaacg   1020

gctcacaatg agtgtgacat tagaaaactc cttgcagagg agagtttctc caggctcttc   1080

ctggggcctt agatctgcag ttccgacaag ctt                                1113
```

```
<210> SEQ ID NO 17
<211> LENGTH: 1089
<212> TYPE: DNA
<213> ORGANISM: Mus musculus
<220> FEATURE:
<221> NAME/KEY: misc_feature
<223> OTHER INFORMATION: Anti-sense RNA complementary to sequences
      specific for mouse TrkB.T1

<400> SEQUENCE: 17

cggttagcag agggcaatgg aaagggacaa gattttaatt ccctatatgc atataccccta     60

ccattattta ttctcaggct gtggttaatt caggtccata ctcctggcca cacagtccct    120

ggtgctgctc cgttctacct gccgggtgga ctttgaaagc aatcgttagc gaagagtttg    180

ggtctttgct gccagcaaaa caaagaacct actaatgaca ccaccaatgt gcctttaagt    240

ctatcagtcg cagggttgta ggtggaaatc acagaagtta gcaaaggtta gagaacagaa    300

gatgttgctg aaataggtgt tatgtgtgga ttagactttt agtgtgcact tagacctagc    360

tatgacttta gatagatgac agatagatag atagatagat agatagatag atagatagat    420

agatgataga taagtaaatc gatgataggt agatagatag atgatagata agtagatcga    480

tgataggtag atagatgata gatagataga tagatagata gatagataga tagatagata    540

gatagataga tagacagaca gatagatatg atagagaggt aggtagatag atgatagaca    600

gatagacaga cagatagata tgatagacaa acagatagat ggatagatga tagatgcaga    660

gtttttaatt tgcaaatcac ctttaataaa cagaagcaat taatgtcagc acattttccg    720

tatagtcaaa cagctcgctt ttcattagag aggcataatc caatgagatt tcacttcgat    780

tctatatttg aactattgta agaacagaag gtgaatctaa gtgtgttctt ctgctgcttc    840

tcagctgcct gacccctgcc tctgccttgg ggttccccag tcacagctca caacaagcag    900

gctgcagaca tcctcggaga ttacccattt ccaccagaca ccctcaaata agcagcactt    960

cctgggatag gcaacagcag tcccagagtt cagctcacag ggcgtcaggc aacaagcacc   1020

acagccccag cctttgtctt tcctttatct cagctaccca tccagtggga tcttatgaaa   1080

caaaacaaa                                                          1089

<210> SEQ ID NO 18
<211> LENGTH: 20
<212> TYPE: RNA
<213> ORGANISM: Mus musculus
<220> FEATURE:
<221> NAME/KEY: misc_feature
<223> OTHER INFORMATION: Anti-sense RNA for mouse TrkB.T1

<400> SEQUENCE: 18

aagcaggcug cagacauccu                                                 20
```

-continued

<210> SEQ ID NO 19
<211> LENGTH: 359
<212> TYPE: DNA
<213> ORGANISM: Homo sapiens
<220> FEATURE:
<221> NAME/KEY: misc_feature
<223> OTHER INFORMATION: Anti-sense RNA specific for human TrkB.T1

<400> SEQUENCE: 19

```
agagaagtac aatccaatgg gatttcattt cagttttgta tttgaactac tgtaagaaga     60

gaagcattaa tttaacatgt tttcttgagg tgctgcttag ctgcctgaga gttacctctg    120

cattggtgtt ccccaatcac agctcacagt atatgcaggc ttcatatagt acagcctcca    180

aacaccgccc acatctacca gaaaacccca gataagcagc acttcccggg ataagccaac    240

agcagtccca ggagtccagc ttacatggca gcatcaacca acaagcacca cagccccttt    300

ctctgtcttt tcctttattt cagctaccca tccagtggga tcttatgaaa caaaacaaa     359
```

<210> SEQ ID NO 20
<211> LENGTH: 296
<212> TYPE: DNA
<213> ORGANISM: Homo sapiens
<220> FEATURE:
<221> NAME/KEY: misc_feature
<223> OTHER INFORMATION: Anti-sense RNA complementary to Exon 19 of Human TrkB.Shc

<400> SEQUENCE: 20

```
ctccatcttg ccatcctgat tgatcgagga gatgggtcta tagttaaagt ggcatagtac     60

tttgaggggt tagtcattag agcacactgc tttgtcttgg aaaggcaact tcttgcttgg    120

ctaggttatg gaagctaagg agtgacgtca agatgttgtc tggccagaat ttgcagataa    180

ccatagaact cttctcctcc atcaggcatg gatttagcct cctttagttc ctgcagtgac    240

acaggagcct ccaaatacca aattattatc aggcggtctt gggggaacct ctgggc        296
```

<210> SEQ ID NO 21
<211> LENGTH: 1030
<212> TYPE: DNA
<213> ORGANISM: Homo sapiens
<220> FEATURE:
<221> NAME/KEY: misc_feature
<223> OTHER INFORMATION: Anti-sense RNA complementary to human truncated TrkC exon 13B

<400> SEQUENCE: 21

```
aagcttcctc ccctggaaga cactccttta atttaaggga ttttttagt accaaatccc      60

gtgctgggca cctagtcgta cctcagtcca cgaaatatat ggaggcttga tgagtcttaa    120

ggtcttaaga accaaaattg gttaggggag ggatctttac tgcatacaaa gacgtcaaag    180

gaggtaactc accatgtgac cttgggtaag acacttcccc actctggacc tcaggttcct    240

catatatata gtgagttgat gggactagat gatctctatt gtccttcaag tttaatatcc    300

catgattgtc tatgtttgaa aagacccctg gcagaagagg cagacatggg ggaattaatg    360

gtcagtatta aaccccaagt gcaaaaaaca tgggaaagta tttttcttaa gtgcacaatg    420

ccagaaacag aaatccaggt ttctcagctc ctgtacccac tctgctgtgc ctgtagtggc    480

agctggttta ttttacgcat aaaatctaga tcctaagaat ctcaccctgg cattatagaa    540

atggcacaag ttagagtcag agaagaaaga ttcaccatca ccatgaactc tgtcctgcac    600

ttttcctaac atatttgccc ccattttcct tcttggacca gaatgtctca aaatggtgcc    660
```

-continued

```
catcattgcc attcagagtg tcattcctgg gcctggatgg atgtttcttc tgacttggga    720

gataatcctg gacccaagac cctctttctg gcttctaata tcccatcaaa aaaattcagc    780

taattttcaa gaggaaagca atgtgacaag gcggggatga tgaggagatg agaggaggtg    840

gtggtgtttg gttccttaaa atcttccttg ccattgttag ggcataaacc attggaaaaa    900

ccaaagctgt tagctcactg aagacctgaa gactacaact tctataaaga gatatcattg    960

tagcttctga ggatgaaatc tcctttggag accatgcagc atttgtgggc cctggaaaga   1020

tccgtgtcgg                                                          1030


<210> SEQ ID NO 22
<211> LENGTH: 1113
<212> TYPE: DNA
<213> ORGANISM: Homo sapiens
<220> FEATURE:
<221> NAME/KEY: misc_feature
<223> OTHER INFORMATION: Anti-sense RNA complementary to human truncated
      TrkC exon 14B

<400> SEQUENCE: 22

aagcttgtcg gaactgcaga tctaaggccc caggaagagc ctggagaaac tctcctctgc     60

aaggagtttt ctaatgtcac actcattgtg agccgttcca gagagaagag gaagtagggg    120

gcaagtatgt cccaaaaaag gatgattttt ccaccgaaaa taaaaataaa aatgtaaagt    180

gattggtttc cattctttcc tctgagacct aacttggtgc caatacttga gcctggctcc    240

ccctcctctt accgcgccgt ctccacctct gcttaggtgc tctctgtgac tcttccccac    300

tggaggttgc agggcgacga ggtcactaag aggacagcat ggtatcctgg gagagccagg    360

gagaccccac gcttccaagc agggaaagtg aggctggagc acggctggac ttcatcaggc    420

tttcttgtga tggttaggtt gtttttgtaa agcaagagaa tggctagtgt atttaaaaga    480

tgctcctggt gcacaggttt ttaattctct ttattggctc taaagatagt ggcaggagct    540

gcctcgtagg ccgggaaaaa aggagcacag tgatgattgg agggaagggg caaccctgcc    600

agtggtggat gggggaaaac acccatctgg tggtgttaaa gggtgccggg gcactggtgg    660

ctcatgcagt ttctacttag catccctgga tccaaagaga acaatgccta gagcttccaa    720

cctctcagag ggcccagcct accaaggtga catcaaaaca aggaggctta aaaggagttt    780

ttaaaagcca tgacgtcctt tgctgaaata aacattgaca tcctcaacat agatgccatg    840

gttaagaggc ttggaatgtc cgggaaggct tattggattc aacataattt ctctgaaacc    900

tataaaaaac aaaaagaaaa aaaaacagaa aaaagcaaaa taaagtaaaa accaaaaccc    960

ccaaagaaga tcaaaactag gaggggaaat agagagggag cttgaaaggg gaagaactgt   1020

cagcaaaagg gaaggatagg aggaggggat taacttaaaa ccctgcatgg tcagagaaac   1080

tggaaacact ccattttgct gcagcctcca ctg                                1113
```